United States Patent [19]

Karanewsky et al.

[11] 4,432,971
[45] Feb. 21, 1984

[54] PHOSPHONAMIDATE COMPOUNDS

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 392,977

[22] Filed: Jun. 28, 1982

Related U.S. Application Data

[63] Continuation-in-part of Ser. No. 289,671, Aug. 31, 1981, abandoned.

[51] Int. Cl.$^3$ .................. A61K 31/675; A61K 37/00; C07F 9/65
[52] U.S. Cl. ............... 424/177; 260/112.5 R; 424/200; 546/21; 546/22; 546/23; 548/112; 548/119; 548/409; 548/413; 548/414
[58] Field of Search ............... 260/112.5 R; 548/409, 548/119, 112, 413, 414; 424/177, 200; 546/21, 22, 23

[56] References Cited

U.S. PATENT DOCUMENTS

| | | | |
|---|---|---|---|
| 4,053,651 | 11/1977 | Ondetti et al. | 424/319 |
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 260/326.2 |
| 4,154,935 | 5/1979 | Ondetti et al. | 546/189 |
| 4,168,267 | 9/1979 | Petrillo | 260/326.2 |
| 4,192,878 | 3/1980 | Ondetti | 424/270 |
| 4,199,512 | 4/1980 | Ondetti et al. | 260/326.12 R |
| 4,217,359 | 8/1980 | Krapcho | 424/274 |
| 4,234,489 | 11/1980 | Ondetti et al. | 260/326.42 |
| 4,256,751 | 3/1981 | Hayashi et al. | 424/258 |
| 4,256,761 | 3/1981 | Suh et al. | 424/282 |
| 4,296,033 | 10/1981 | Petrillo et al. | 260/326.2 |
| 4,296,113 | 10/1981 | Ondetti | 424/246 |
| 4,310,461 | 1/1982 | Krapcho et al. | 260/326.2 |
| 4,311,697 | 1/1982 | Krapcho | 424/240 |
| 4,316,896 | 2/1982 | Thorsett et al. | 424/200 |
| 4,316,905 | 2/1982 | Krapcho | 424/274 |
| 4,316,906 | 2/1982 | Ondetti et al. | 424/274 |
| 4,337,201 | 6/1982 | Petrillo | 548/413 |
| 4,379,146 | 4/1983 | Greenlee et al. | 424/177 |

FOREIGN PATENT DOCUMENTS

| | | |
|---|---|---|
| 868532 | 6/1978 | Belgium . |
| 2027025 | 2/1980 | United Kingdom . |
| 2048863 | 12/1980 | United Kingdom . |

OTHER PUBLICATIONS

Galardy, "Inhibition of Angiotensin . . . ", *Biochem Biophs Res. Comm.*, 1980, vol. 97, pp. 94–99.
Mauger, "Analogs and Homologs of Proline . . . ", *Chem. Review*, vol. 66, pp. 47–86 (1966).
Thorsett et al., "Phosphorus Containing Inhibitors . . . ", 182 National Meeting, ACS, New York, Aug. 1981, MEDI-7.

*Primary Examiner*—Richard Raymond
*Attorney, Agent, or Firm*—Lawrence S. Levinson; Stephen B. Davis

[57] ABSTRACT

Phosphonamidates of the formula

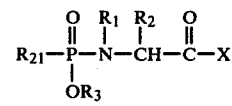

wherein X is a substituted or unsubstituted imino or amino acid or ester. These compounds possess angiotensin converting enzyme activity and are thus useful as hypotensive agents.

10 Claims, No Drawings

PHOSPHONAMIDATE COMPOUNDS

RELATED APPLICATION

This application is a continuation-in-part of U.S. Ser. No. 289,671 filed Aug. 3, 1981, now abandoned.

BACKGROUND OF THE INVENTION

Thorsett, et al. in European Patent Application Ser. No. 9,183 disclose phosphoryl derivatives of aminoacids including proline. These compounds are disclosed as being hypotensive agents due to their angiotensin converting enzyme inhibition activity.

Petrillo in U.S. Pat. No. 4,168,267 discloses that various phosphinylalkanoyl substituted prolines are useful as hypotensive agents due to their ability to inhibit the angiotensin converting enzyme.

Ondetti, et al. in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti, et al. in U.S. Pat. No. 4,105,776 disclose such compounds wherein the proline ring is unsubstituted or substituted by an alkyl or hydroxy group. Ondetti, et al. in U.S. Pat. No. 4,154,935 disclose such compounds wherein the proline ring is substituted with one or more halogens. Ondetti, et al. in U.K. patent application No. 2,028,327 and U.S. Pat. No. 4,316,906 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.K. patent application No. 2,039,478 and U.S. Pat. No. 4,311,697 disclose compounds wherein the proline ring has a diether, dithioether, ketal or thioketal substituent in the 4-position. Krapcho in U.S. Ser. No. 164,985 filed July 1, 1980, now U.S. Pat. No. 4,316,905, discloses such compounds wherein the proline ring has a cycloalkyl, phenyl, or phenyl-lower alkylene substituent. Ondetti, et al. in U.S. Pat. No. 4,234,489 disclose such compounds wherein the proline has a keto substituent in the 5-position. Krapcho, et al. in U.S. Ser. No. 162,341 filed June 23, 1980, now U.S. Pat. No. 4,310,461, disclose such compounds wherein the proline has an imido, amido, or amino substituent in the 4-position. Iwao, et al. in U.K. patent application No. 2,027,025 disclose such compounds wherein the proline has an aromatic substituent in the 5-position. Ondetti, et al. in U.S. Pat. Nos. 4,053,651 and 4,199,512 disclose that mercaptoacyl derivatives of various aminoacids other than proline are also useful angiotensin converting enzyme inhibitors.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Patent No. 868,532.

Mercaptoacyl derivatives of dihydroisoindole carboxylic acids and tetrahydroisoquinoline carboxylic acids are disclosed as being useful hypotensive agents by Ondetti, et al. in U.S. Ser. No. 69,031, filed Aug. 23, 1979. These mercaptoacyl tetrahydroisoquinoline compounds are also disclosed by Portlock in U.K. application No. 2,048,863 and by Hayashi et al. in U.S. Pat. No. 4,256,751.

SUMMARY OF THE INVENTION

This invention is directed to new phosphonamidate substituted amino or imino acids of formula I and salts thereof

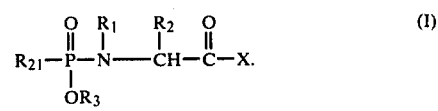

X is an imino or amino acid of the formula

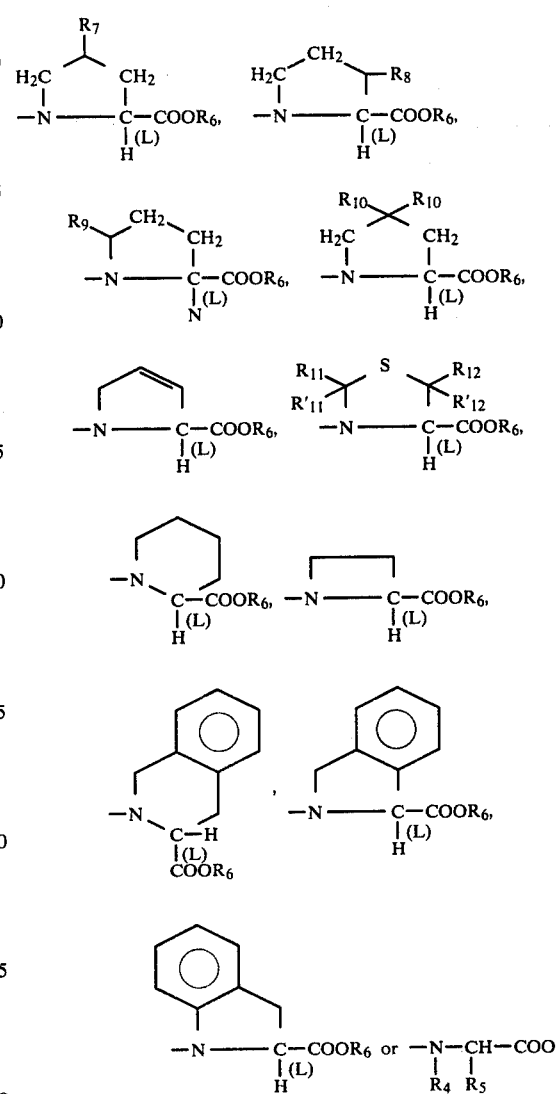

$R_7$ is hydrogen, lower alkyl, halogen, keto, hydroxy

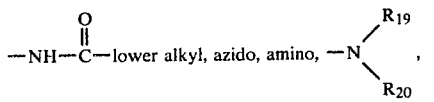

-continued $-NH-\overset{\overset{O}{\|}}{C}-(CH_2)_m-\underset{(R_{14})_p}{\bigcirc}$, $-(CH_2)_m-\underset{(R_{13})_p}{\bigcirc}$, $-(CH_2)_{\overline{m}}-\underset{O}{[\![}\phantom{x}]\!]$, $-(CH_2)_{\overline{m}}-\underset{S}{[\![}\phantom{x}]\!]$, $-(CH_2)_{\overline{m}}-\underset{N}{\bigcirc}$ a 1- or 2-naphthyl of the formula $-(CH_2)_m\underset{2}{\overset{1}{\bigcirc\!\bigcirc}}-(R_{14})_{p'}$, $-(CH_2)_m-$cycloalkyl, $-O-\overset{\overset{O}{\|}}{C}-N\overset{R_{15}}{\underset{R_{15}}{\big\langle}}$, $-O-$lower alkyl, $-O-(CH_2)_{\overline{m}}-\underset{(R_{13})_p}{\bigcirc}$, a 1- or 2-naphthyloxy of the formula $-O-(CH_2)_m\underset{2}{\overset{1}{\bigcirc\!\bigcirc}}-(R_{14})_{p'}$, $-S-$lower alkyl, $-S-(CH_2)_m-\underset{(R_{13})_p}{\bigcirc}$, or a 1- or 2-naphthylthio of the formula $-S-(CH_2)_m\underset{2}{\overset{1}{\bigcirc\!\bigcirc}}-(R_{14})_{p'}$.

$R_8$ is keto, halogen, $-O-\overset{\overset{O}{\|}}{C}-N\overset{R_{15}}{\underset{R_{15}}{\big\langle}}$, $-O-(CH_2)_m-\underset{(R_{13})_p}{\bigcirc}$, —O—lower alkyl, a 1- or 2-naphthyloxy of the formula $-O-(CH_2)_m\underset{2}{\overset{1}{\bigcirc\!\bigcirc}}-(R_{14})_{p'}$, $-S-$lower alkyl, $-S-(CH_2)_m-\underset{(R_{13})_p}{\bigcirc}$, or a 1- or 2-naphthylthio of the formula $-S-(CH_2)_m\underset{2}{\overset{1}{\bigcirc\!\bigcirc}}-(R_{14})_{p'}$.

$R_9$ is keto or $-(CH_2)_m-\underset{(R_{13})_p}{\bigcirc}$.

$R_{10}$ is halogen or $-Y-R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is $-\underset{(R_{14})_p}{\bigcirc}$.

$R_{13}$ is hydrogen, lower alkyl of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons, $-(CH_2)_m-\underset{(R_{13})_p}{\bigcirc}$, or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl, $-(CH_2)_m-$cycloalkyl, or $-(CH_2)_m-\underset{(R_{14})_p}{\bigcirc}$.

$R_5$ is hydrogen, lower alkyl,

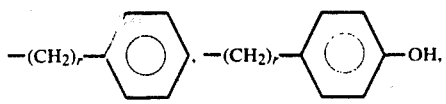

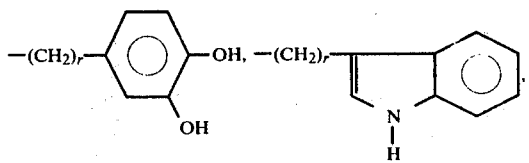

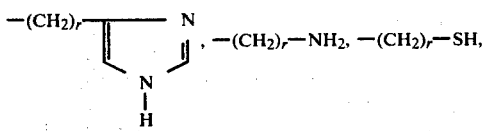

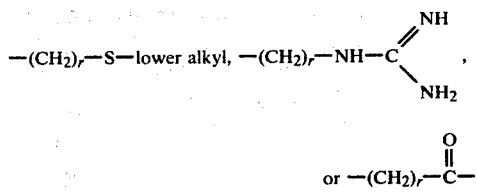

r is an integer from 1 to 4.
R₁ is hydrogen, lower alkyl, or cycloalkyl.
R₂ is hydrogen, lower alkyl, halo substituted lower alkyl,

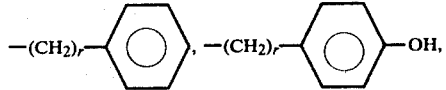

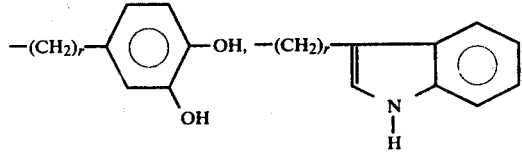

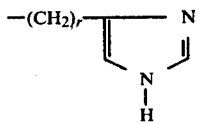

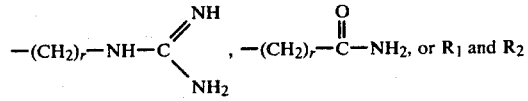

or R₁ and R₂ taken together are —(CH₂)ₙ— wherein n is an integer from 2 to 4.
R₃ and R₆ are independently selected from hydrogen, lower alkyl, benzyl, benzhydryl, or

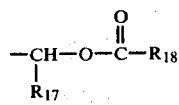

wherein $R_{17}$ is hydrogen, lower alkyl, cycloalkyl, or phenyl, and $R_{18}$ is hydrogen, lowr alkyl, lower alkoxy, phenyl, or $R_{17}$ and $R_{18}$ taken together are

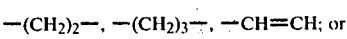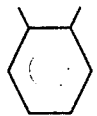

$R_{19}$ is lower alkyl, benzyl, or phenethyl.
$R_{20}$ is hydrogen, lower alkyl, benzyl or phenethyl.
$R_{21}$ is alkyl of 1 to 10 carbons,

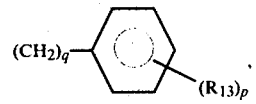

—(CH₂)_q—cycloalkyl,

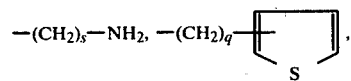

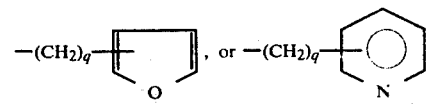

wherein q is zero or an integer from 1 to 7, s is an integer from 1 to 8, and $R_{13}$, and p are as defined above.

DETAILED DESCRIPTION OF THE INVENTION

This invention in its broadest aspects relates to the phosphonamidate substituted imino or amino acid compounds of formula I above, to compositions containing such compounds and to the method of using such compounds as anti-hypertensive agents.

The term alkyl used in defining $R_{21}$ refers to straight or branched chain hydrocarbon radicals having up to ten carbons, for example, methyl, ethyl, propyl, ispropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to lower alkyl groups in which one or more hydrogens have been replaced by —NH₂, i.e. aminomethyl, 2-aminoethyl, etc.

The symbols

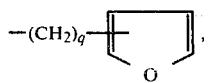

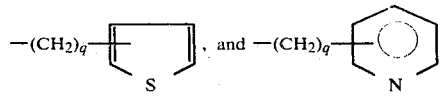

represent that the alkylene bridge is attached to an available carbon atom.

The compounds of formula I wherein $R_{21}$ is other than $-(CH_2)_s-NH_2$ are prepared according to the following procedures. A phosphonochloridate of formula II wherein $R_3$ is lower alkyl, benzyl or benzhydryl

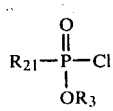 (II)

is coupled with a peptide ester of the formula

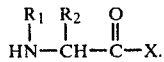 (III)

Preferably, the peptide ester of formula III is in its hydrochloride salt form and $R_6$ in the definition of X is lower alkyl, benzyl or benzhydryl.

These compounds of formula I can also be prepared by coupling an acid or its activated form of formula IV wherein $R_3$ is lower alkyl, benzyl or benzhydryl

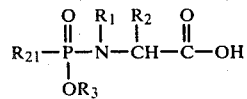 (IV)

with an imino or amino acid or ester of the formula

HX. (V)

The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

In the above reactions if $R_5$ and/or $R_2$ is

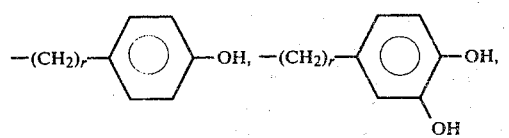

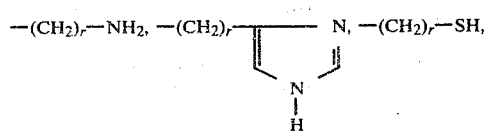

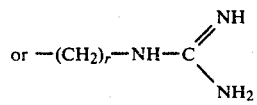

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The products of formula I wherein either or both of $R_3$ and $R_6$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_6$ are hydrogen.

The ester products of formula I wherein $R_6$ is

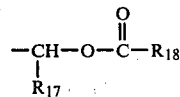

may be obtained by employing the peptide of formula III or the imino or amino acid of formula V in the above reactions with the ester group already in place. Such ester reactants can be prepared by treating peptide, imino, or amino acids with an acid chloride such as

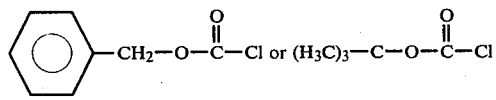

so as to protect the N-atom. The protected acid compound is then reacted in the presence of base with a compound of the formula

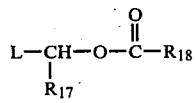 (VI)

wherein L is a leaving group such as chlorine, bromine, tolylsulfonyloxy, etc., followed by removal of the N-protecting group such as by treatment with acid or hydrogenation.

The ester products of formula I wherein $R_6$ is

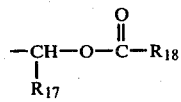

can also be obtained by treating the product of formula I wherein $R_6$ is hydrogen with a molar equivalent of the compound of formula VI. The diester products wherein $R_3$ and $R_6$ are the same and are

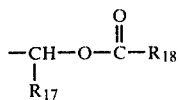

can be obtained by treating the product of formula I wherein $R_3$ and $R_6$ are both hydrogen or an alkali metal salt with two or more equivalents of the compound of formula VI.

The ester products of formula I wherein $R_3$ is

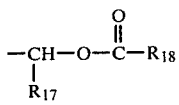

can be obtained by treating the product of formula I wherein $R_3$ is hydrogen or an alkali metal salt and $R_6$ is benzyl or benzhydryl with the compound of formula VI in the presence of base. Removal of the $R_6$ ester group such as by hydrogenation yields the products of formula I wherein $R_3$ is

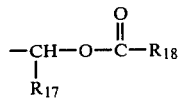

and $R_6$ is hydrogen.

The products of formula I wherein $R_7$ is amino may be obtained by reducing the corresponding products of formula I wherein $R_7$ is azido.

The phosphonamidate reactants of formula IV can be prepared by coupling the phosphonochloridate of formula II wherein $R_3$ is lower alkyl, benzyl, or benzhdryl with the amino acid ester such as the benzyl or benzhydryl ester of the formula $$\overset{R_1}{\underset{|}{HN}}-\overset{R_2}{\underset{|}{CH}}-\overset{O}{\underset{\|}{C}}-\text{ester.} \qquad \text{(VII)}$$

The phosphonochloridates of formula II are described in the literature and in particular by Kosolapoff, et al. in Organic Phosphorous Compounds, Vol. 7, Chapter 18 (Wiley 1972).

The various peptides of formula III and imino and amino acids and esters of formula V are described in the literature and in the various patents and pending U.S. application referred to above. Various substituted prolines are also disclosed by Mauger et al., Chem. Review, Vol. 66, p. 47-86 (1966). When the amino or imino acid is known, it can be readily converted to the ester by conventional means. For example, the esters where $R_6$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_6$ is benzyl can be obtained by treating the imino acid with benzyl alcohol and thionyl chloride.

As disclosed by Krapcho in U.S. Ser. No. 164,985, now U.S. Pat. No. 4,316,905, the substituted prolines wherein $R_7$ is

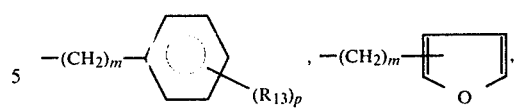

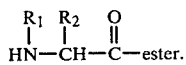

are prepared by reacting a 4-keto proline of the formula

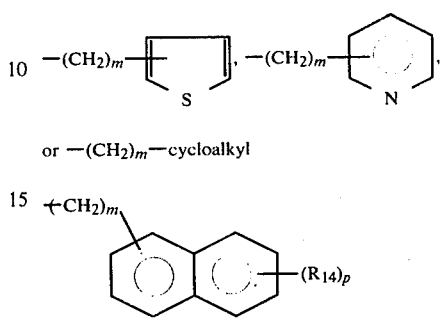

with a solution of the Grignard or lithium reagent $$R_7\text{—Mg—halo or } R_7\text{—Li} \qquad \text{(IX)}$$

wherein $R_7$ is as defined above and halo is Br or Cl to yield

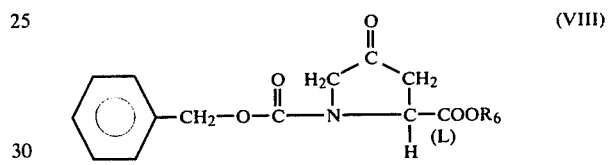

This compound is treated with a dehydrating agent such as p-toluenesulfonic acid, sulfuric acid, potassium bisulfate, or trifluoroacetic acid to yield the 3,4-dehydro-4-substituted proline of the formula

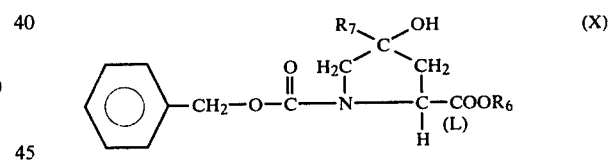

Removal of the N-benzyloxycarbonyl protecting group and hydrogenation of the compound of formula XI yields the desired starting materials. The substituted proline wherein $R_7$ is cyclohexyl can be prepared by further hydrogenation of the 4-phenyl proline compound.

The substituted prolines wherein $R_7$ is the substituted amino group

may be prepared by reacting a 4-keto proline of formula VIII with the amine

in the presence of hydrogen and catalyst or in the presence of sodium cyanotrihydridoborate.

The compounds of formula I wherein $R_{21}$ is —(CH$_2$)$_s$—NH$_2$ are prepared by reacting a phthalidyl protected compound of the formula

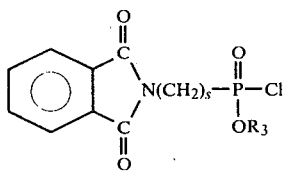

(XII)

wherein $R_3$ is lower alkyl, benzyl, or benzhydryl with the peptide ester of formula III, preferably wherein $R_6$ in the definition of X is benzyl, in the presence of triethylamine to yield the protected compound of formula

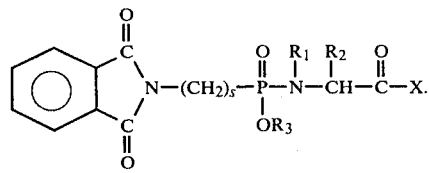

(XIII)

Treatment with hydrazine removes the phthalidyl protecting group after which the $R_3$ and $R_6$ ester group can be removed as described previously to yield the corresponding diacid compounds of formula I.

The phosphonochloridates of formula XII can be prepared by treating a phthalidyl protected alkylbromide of the formula

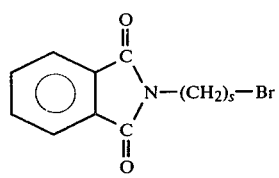

(XIV)

with a trialkylphosphite of the formula

 (XV)

to yield the diester of the formula

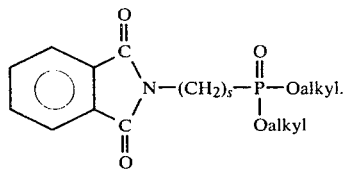

(XVI)

Treatment of this diester with trimethylsilylbromide yields the phosphonic acid of the formula

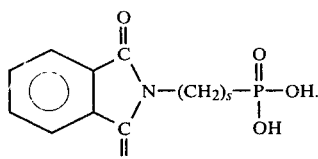

(XVII)

The acid of formula XVII can then be treated with phosphorus pentachloride and an alcohol of the formula $R_3$—OH (XVIII)

in the presence of triethylamine to give the compound of formula XII.

Preferred compounds of this invention with respect to the amino or imino acid or ester part of the structure of formula I are those wherein:

$R_4$ is hydrogen, methyl, cyclohexyl, phenyl or benzyl.

$R_5$ is hydrogen, lower alkyl of 1 to to 4 carbons,

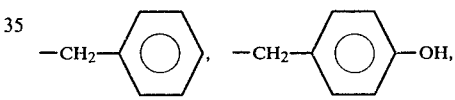

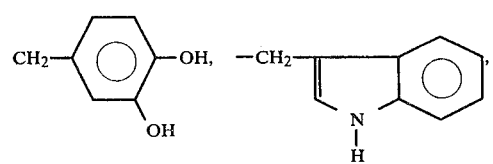

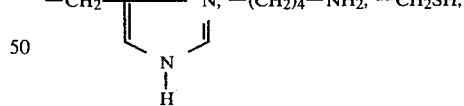

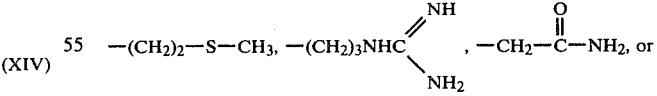

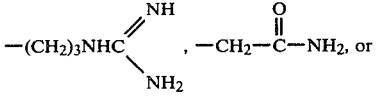

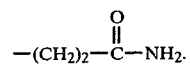

$R_6$ is hydrogen, an alkali metal salt, or

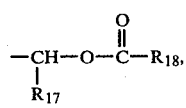

$R_{17}$ is hydrogen, straight or branched chain lower alkyl of 1 to 4 carbons, or cyclohexyl and $R_{18}$ is straight or branched chain lower alkyl of 1 to 4 carbons or phenyl.

$R_7$ is hydrogen.

$R_7$ is hydroxy.

$R_7$ is chloro or fluoro.

$R_7$ is lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

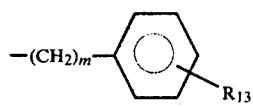

wherein m is zero, one or two, $R_{13}$ is hydrogen, methyl, methoxy, methylthio, chloro, bromo, fluoro, or hydroxy.

$R_7$ is

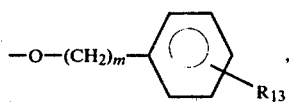

1-naphthyloxy, or 2-naphthyloxy wherein m is zero, one or two, and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

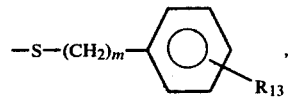

1-naphthylthio, or 2-naphthylthio wherein m is zero, one or two, and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

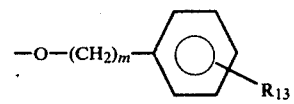

wherein m is zero, one or two, and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

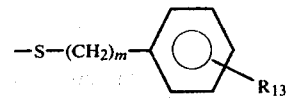

wherein m is zero, one or two, and $R_{13}$ is hydrogen, methyl, methoxy, methylthio, chloro, bromo, fluoro, or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain alkyl of 1 to 4 carbons or the $R_{16}$ groups join to complete an unsubstituted 5- or 6-membered ring or said ring in which one or more of the carbons has a methyl or dimethyl substituent.

$R_{11}$, $R_{11}'$, $R_{12}$ and $R_{12}'$ are all hydrogen, or $R_{11}$ is phenyl, 2-hydroxyphenyl or 4-hydroxyphenyl and $R_{11}'$, $R_{12}$ and $R_{12}'$ are hydrogen.

Most preferred compounds of this invention with respect to the amino or imino acid or ester part of the structure of formula I are those wherein:

X is

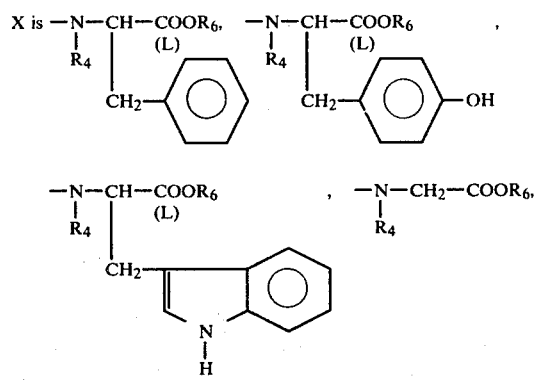

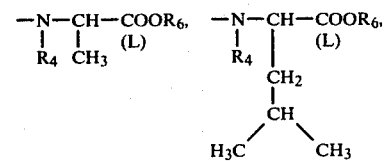

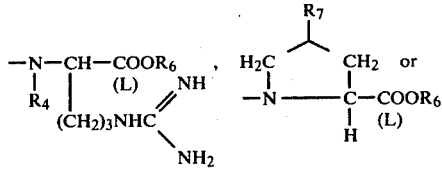

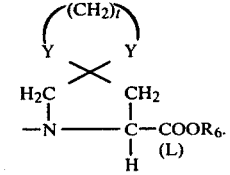

$R_4$ is hydrogen, methyl, cyclohexyl, phenyl or benzyl.

$R_6$ is hydrogen,

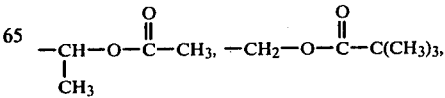

-continued

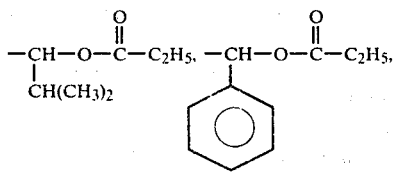

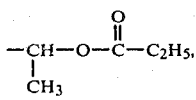

or an alkali metal salt.

$R_7$ is hydrogen.

$R_7$ is cyclohexyl.

$R_7$ is lower alkoxy of 1 to 4 carbons.

$R_7$ is

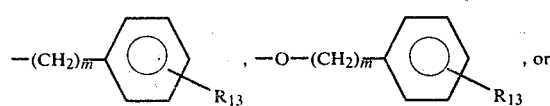

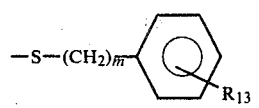

wherein m is zero, one, or two and $R_{13}$ is hydrogen, methyl, methoxy, methylthio, Cl, Br, F or hydroxy.

Y is oxygen or sulfur and t is two or three, especially wherein Y is sulfur and t is two.

Preferred compounds of this invention with respect to the phosphonamidate alkanoyl sidechain of the structure of formula I are those wherein:

$R_1$ is hydrogen or lower alkyl of 1 to 4 carbons, especially hydrogen or methyl.

$R_2$ is hydrogen, lower alkyl of 1 to 4 carbons, $CF_3$, or amino substituted lower alkyl of 1 to 4 carbons, especially hydrogen, methyl or $-(CH_2)_4NH_2$, or $R_1$ and $R_2$ taken together are $-(CH_2)_3-$.

$R_3$ is hydrogen, an alkali metal salt, lower alkyl of 1 to 4 carbons, or

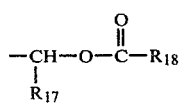

wherein $R_{17}$ is hydrogen, straight or branched chain lower alkyl of 1 to 4 carbons, or cyclohexyl and $R_{18}$ is straight or branched chain lower alkyl of 1 to 4 carbons or phenyl, especially hydrogen, alkali metal salt, ethyl,

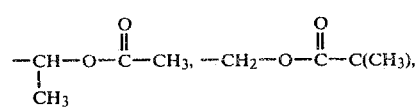

-continued

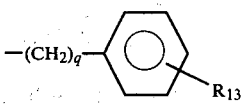

$R_{21}$ is alkyl of 1 to 10 carbons;

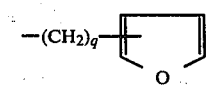

wherein q is zero or an integer from 1 to 4 and $R_{13}$ is hydrogen, methyl, methoxy, methylthio, chloro, bromo, fluoro, or hydroxy; $-(CH_2)_q-$cycloalkyl wherein cycloalkyl is of 5 or 6 carbons and q is zero or an integer from 1 to 4;

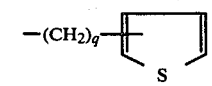

wherein q is zero or an integer from 1 to 4;

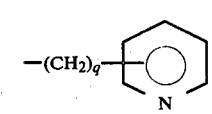

wherein q is zero or an integer from 1 to 4;

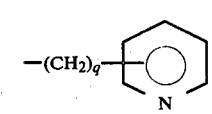

wherein q is zero or an integer from 1 to 4; or $-(CH_2)_s-NH_2$ wherein s is an integer from 1 to 8.

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

As shown above, the amino or imino acid or ester portion of the molecule of the products of formula I represented by X is in the L-configuration. Depending upon the definition of $R_2$ and $R_{17}$ other asymmetric center may be present in the phosphonamidate alkanoyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→ angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrenedivinyl benzene polymer resin.

EXAMPLE 1

1-[N-[Hydroxy(4-phenylbutyl)phosphinyl]-L-alanyl]-L-proline, dilithium salt (a) t-Butoxycarbonyl-L-alanyl-L-proline, phenylmethyl ester A solution of t-butoxycarbonyl-L-alanine (2.48 g., 13.1 mmole) in 23 ml. of dry chloroform at $-15°$ (ice-salt bath) is treated with N-methylmorpholine (1.47 ml., 13.1 mmole) followed by isobutyl chloroformate (1.8 ml., 13.1 mmole) to give a precipitate. After 15 minutes, L-proline, phenylmethyl ester, hydrochloride salt (3.18 g., 13.1 mmole) and N-methylmorpholine (1.47 ml., 13.1 mmole) are added. Gas evolution ensues and the mixture is kept below $-10°$ for one hour, then allowed to warm to room temperature, and stirred overnight under argon. The mixture is diluted with ethyl acetate, filtered, and the filtrate evaporated to dryness. The residue is taken up in ethyl acetate and washed successively with 5% potassium bisulfate, saturated sodium bicarbonate, saturated sodium chloride, dried ($Na_2SO_4$) and evaporated. The residue is purified by flash chromatography on silica gel (210 g.) eluting with ethyl acetate/hexane (1:2) to give t-butoxycarbonyl-L-alanyl-L-proline, phenylmethyl ester (4.37 g.) as a colorless oil; $R_f$ (ethyl acetate/hexane, 1:1) is 0.47.

(b) L-Alanyl-L-proline, phenylmethyl ester, hydrochloride salt t-Butoxycarbonyl-L-alanyl-L-proline, phenylmethyl ester (4.37 g., 11.6 mmole), prepared as set forth in part (a), is dissolved in 15 ml. of trifluoroacetic acid and stirred at room temperature for 15 minutes. The mixture is then evaporated to dryness, taken up in 30 ml. of dry ethyl ether and treated with ethyl ether saturated with dry hydrochloric acid in small portions until no further precipitate forms. The white solid precipitate is collected, washed thoroughly with ethyl ether and dried in vacuo to give 3.32 g. of L-alanyl-L-proline, phenylmethyl ester, hydrochloride salt as a white solid; m.p. 172°; $R_f$(dichloromethane/acetic acid/methanol, 8:1:1) is 0.49.

(c) (4-Phenylbutyl)phosphinic acid, phenylmethyl ester

A mixture of 4-phenyl-1-butene (13.2 g., 0.1 mole) and sodium hypophosphite monohydrate (15.8 g., 0.149 mole) in 25 ml. of methanol is treated with 1 ml. of di-t-butylperoxide and heated in an autoclave at 130°-135° for 7 hours. The cooled mixture is then diluted with water, adjusted to pH 8 with 1 N sodium hydroxide, and extracted with ethyl ether. The ethyl ether extract is discarded and the aqueous phase is acidified to pH 1 with concentrated hydrochloric acid and extracted with ethyl acetate. The ethyl acetate extracts are washed successively with water, saturated sodium chloride, dried ($Na_2SO_4$) and evaporated to give 19.4 g. of crude (4-phenylbutyl)phosphinic acid as a colorless oil. Tlc (dichloromethane/acetic acid/methanol 20:1:1) major spot at $R_f$ 0.37.

19

A mixture of this crude phosphinic acid (4.3 g., 21.7 mmole), benzylbromide (3.1 ml., 26.1 mmole), and powdered anhydrous potassium carbonate (6.0 g., 43.5 mmole) in 40 ml. of dry toluene and 10 ml. of dry dimethylformamide is refluxed under argon for 3 hours. The cooled mixture is diluted with ethyl acetate and washed successively with water, saturated sodium bicarbonate, saturated sodium chloride, dried ($Na_2SO_4$) and evaporated. The crude product is purified by Kugelrohr distillation. After a small amount of low boiling material, the main fraction distills at 210°–230° (0.1 mm. of Hg) giving 3.13 g. of (4-phenylbutyl) phosphinic acid, phenylmethyl ester as a colorless liquid. Tlc (ethyl acetate) shows virtually a single spot at $R_f$ 0.52.

(d)
1-[N-[Phenylmethoxy(4-phenylbutyl)phosphinyl]-L-alanyl]-L-proline, phenylmethyl ester A half saturated solution of dry chlorine in carbon tetrachloride is added dropwise by syringe to a solution of (4-phenylbutyl)phosphinic acid, phenylmethyl ester (1.0 g., 3.47 mmole), from part (c), in 4 ml. of dry carbon tetrachloride under argon until the yellow color of excess chlorine persits. The mixture is evaporated to dryness (0.1 mm. of Hg), and the colorless residue is taken up in 6 ml. of dry tetrahydrofuran and treated with L-alanyl-L-proline, phenylmethyl ester, hydrochloride salt (1.0 g., 3.2 mmole), from part (b). The resulting suspension is cooled to 0° (ice bath) under argon and treated dropwise with a solution of triethylamine (1.1 ml., 7.95 mmole) in 5 ml. of dry tetrahydrofuran over a 15 minute period. After the addition is complete, the mixture is stirred at 0° for 15 minutes, then allowed to warm to room temperature and stirred for an additional 45 minutes. The mixture is diluted with ethyl acetate, filtered and evaporated to dryness. The residue is taken up in ethyl acetate, washed successively with 5% potassium bisulfate, saturated sodium bicarbonate, saturated sodium chloride, dried ($Na_2SO_4$), and evaporated. The residue is purified by flash chromatography on silica gel (90 g.) eluting first with acetone/dichloromethane (1:8) then acetone/dichloromethane (1:2) to give 1.4 g. of 1-[N-[phenylmethoxy(4-phenylbutyl)phosphinyl]-L-alanyl]-L-proline, phenylmethyl ester as a colorless viscous oil. $R_f$ (acetone/dichloromethane 1:4) is 0.36.

(e)
1-[N-[Hydroxy(4-phenylbutyl)phosphinyl]-L-alanyl]-L-proline, dilithium salt

A solution of the ester product from part (d) (1.2 g., 2.14 mmole) in 36 ml. of methanol is treated with 12 ml. of water, triethylamine (0.9 ml., 6.5 mmole) and 10% palladium-carbon catalyst (0.35 g.) and hydrogenated in a Parr apparatus at an initial pressure of 50 psi. for 1.5 hours. The mixture is filtered through Celite, the filter cake is washed thoroughly with methanol, and the combined filtrate is evaporated to dryness. The residue is taken up in water and applied to an AG-50W-X8(Li+) column (50 ml. settled volume) and eluted with water. Fractions containing the desired material are combined and lyophilized to give 0.82 g. of 1-[N-[hydroxy(4-phenylbutyl)phosphinyl]-L-alanyl]-L-proline, dilithium salt as a white solid. Tlc (isopropanol/concentrated $NH_4OH$/water, 7:2:1) single spot $R_f$ is 0.52.

Anal. Calc'd for $C_{18}H_{25}N_2O_5P \cdot Li_2 \cdot 1.8H_2O$: C, 50.67; H, 6.75; N, 6.56; P, 7.3. Found: C, 50.67; H, 6.38; N, 6.42; P, 7.5.

20

EXAMPLE 2

1-[N-[Ethoxy(4-phenylbutyl)phosphinyl]-L-alanyl]-L-proline, lithium salt (a) (4-Phenylbutyl)phosphonous acid, diethyl ester (4-Chloro-1-oxobutyl)benzene (164 ml., 1 mole), 5% palladium on carbon catalyst (25 g.) and 1 l. of absolute ethanol are shaken in a 2 l. Parr vessel under 40–50 psi of hydrogen for 24 hours. The mixture is filtered and the filtrate is concentrated in vacuo to yield 183 g. of crude product. The crude product is distilled to yield 155 g. of (4-chlorobutyl)benzene.

220 ml. of a solution of (4-chlorobutyl)benzene (1083 g., 6.42 mole) in 1280 ml. of ether is added to a flask containing magnesium (241.6 g., 0.9 mole) in 834 ml. of ether. The mixture is refluxed and a few crystals of iodine are added. The reaction initiates after about 30 minutes. When the initial reaction subsides, the remaining chloride solution is added at a rate sufficient to maintain reflux (addition time about 1.5 hours). Reflux is maintained an additional 2.5 hours and the mixture is cooled and allowed to stir overnight under argon at room temperature to give the Grignard solution, (4-phenylbutyl) magnesium chloride.

Diethylchlorophosphite (914 g., 5.84 mole) and ether (5.12 l.) are combined and cooled to 5°–10°. The (4-phenylbutyl) magnesium chloride solution is added with stirring at a rate sufficient to maintain the reaction temperature below 15° (1.5 hours addition time). The cooling bath is removed and the mixture is stirred 30 minutes at room temperature. The mixture is filtered, the filtrate is concentrated under argon, and the residue is distilled to yield 1120 g. of (4-phenylbutyl) phosphonous acid, diethyl ester; b.p. 114°–119°/0.7 mm.

(b) (4-Phenylbutyl)phosphinic acid, ethyl ester

A mixture of (4-phenylbutyl) phosphonous acid, diethyl ester (6.3 g., 24.8 mmole) and 30 ml. of water is treated with concentrated hydrochloric acid (5 drops) and stirred vigorously at room temperature under an argon atmosphere. After 2 hours, 50 ml. of ethyl acetate is added and stirring continued for an additional 30 minutes. The layers are separated and the organic phase is washed with saturated sodium chloride, dried ($Na_2SO_4$) and evaporated to give 5.6 g. of (4-phenylbutyl) phosphinic acid, ethyl ester as a colorless liquid. Tlc (ethyl acetate, silica gel) single spot $R_f$ is 0.20.

(c)
1-[N-[Ethoxy(4-phenylbutyl)phosphinyl]-L-alanyl]-L-proline, phenylmethyl ester A half saturated solution of dry chlorine in carbon tetrachloride is added dropwise by syringe to a solution of (4-phenylbutyl)phosphinic acid, ethyl ether (0.95 g., 4.2 mmole) in 4 ml. of dry carbon tetrachloride under argon until the yellow color of excess chlorine persists. The mixture is evaporated to dryness (0.1 mm Hg.), the colorless residue is taken up in 6 ml. of dry tetrahydrofuran and treated with L-alanyl-L-proline, phenylmethyl ester, hydrochloride salt (1.0 g., 3.2 mmole). The resulting suspension is cooled to 0° (ice bath) under argon and treated dropwise with a solution of triethylamine (1.1 ml., 7.95 mmole) in 5 ml. of dry tetrahydrofuran over a 15 minute period. After the addition is complete, the mixture is allowed to come to room temperature and stirred for an additional 30 minutes. The mixture is diluted with ethyl acetate, filtered and evaporated to dryness. The residue is taken up in ethyl acetate, washed successively with 5% potassium bisulfate, saturated sodium bicarbonate, saturated sodium chloride, dried ($Na_2SO_4$) and evaporated. The residue is purified by flash chromatography on silica gel (95 g.) eluting first with acetone/hexane (2:3) then acetone/hexane (2:1) to give 1.35 g of 1-[N-[ethoxy(4-phenylbutyl)phosphinyl]-L-alanyl]-L-proline, phenylmethyl ester as a colorless viscous oil. $R_f$ (dichloromethane/acetone, 2:1) is 0.24.

(d) 1-[N-[Ethoxy(4-phenylbutyl)phosphinyl]-L-alanyl]-L-proline, lithium salt A solution of the ester product from part (c) (1.05 g., 2.1 mmole) in 50 ml. of methanol is treated with triethylamine (0.3 ml., 4.1 mmole) and 10% palladium on carbon catalyst (0.25 g.) and hydrogenated in a Parr apparatus at an initial pressure of 45 psi. for 1.5 hours. The mixture is filtered through Celite, the filter cake is washed thoroughly with methanol and the combined filtrates are evaporated to dryness. The residue is taken up in water and applied to an AG-50W-X8 ($Li^+$) column (40 ml. settled volume) and eluted with water. Fractions containing the desired product are combined, millipore filtered, and lyophilized to give 0.75 g. of 1-[N-[ethoxy(4-phenylbutyl)phosphinyl]-L-alanyl]-L-proline, lithium salt as a white solid. Tlc (dichloromethane/methanol/acetic acid, 1:1:20) single spot $R_f$ is 0.44; Tlc (isopropanol/concentrated $NH_4OH$/water, 7:2:1) single spot $R_f$ is 0.69.

Anal. calc'd for $C_{20}H_{30}N_2O_5PLi.2 H_2O$: C, 53.09; H, 7.57; N, 6.19; P, 6.8 Found: C, 53.11; H, 7.27; N, 6.18; P, 6.7.

EXAMPLE 3

1-[N-[Hydroxy(2-phenylethyl)phosphinyl]-L-alanyl]-L-proline, dilithium salt

(a) (2-Phenylethyl)phosphonous acid, diethyl ester

Magnesium metal (4.86 g., 0.2 mole) is slurried in 100 ml. of diethyl ether and treated dropwise with a solution of 2-bromobenzene (37 g., 0.2 mole) in 100 ml. of diethyl ether. Addition is adjusted so as to cause gentle refluxing of the reaction mixture. After addition is complete, the reaction mixture is stirred at room temperature overnight. The mixture is filtered under nitrogen and added dropwise to a chilled 0° solution of diethylchlorophosphite (31.3 g., 0.2 moles) in 60 ml. of diethyl ether so as to keep the internal temperature below 10°. After addition is complete, the reaction mixture is heated at reflux for one hour. The mixture is then chilled, filtered, and concentrated in vacuo. The residue is distilled in vacuo to yield 20 g. of (2-phenylethyl)phosphonous acid, diethyl ester; b.p. 90°–92°/0.05 mm.

(b) (2-Phenylethyl)phosphinic acid, ethyl ester

A mixture of (2-phenylethyl) phosphonous acid, diethyl ester (18 g., 79.6 mmole) and 60 ml. of water is treated with concentrated hydrochloric acid (5 drops) and stirred overnight in an atmosphere of argon. A slight exotherm is observed. The mixture is extracted with ethyl acetate (3×80 ml.), washed with water (2×30 ml.), washed with brine, dried ($MgSO_4$), filtered and the solvent removed to give 15 g. of (2-phenylethyl)phosphinic acid, ethyl ester as a colorless oil. Tlc (ethyl acetate), $R_f$ is 0.16.

(c) (2-Phenylethyl)phosphinic acid

A mixture of (2-phenylethyl)phosphinic acid, ethyl ester (15 g., 75.7 mmole) and 40 ml. of 2 N sodium hydroxide is stirred in an atmosphere of argon for 15 minutes. The solution becomes clear after 5 minutes. The homogeneous solution is washed with ether (2×80 ml.). The aqueous layer is acidified to pH 1 with concentrated hydrochloric acid. The separated oil is extracted with ethyl acetate (2×150 ml.), washed with water (2×50 ml.), washed with brine, dried ($Na_2SO_4$), filtered and the solvent removed to give 9.5 g. of (2-phenylethyl) phosphinic acid as a colorless oil. Tlc (dichloromethane/methanol/acetic acid, 8:1:1) $R_f$ is 0.31.

(d) (2-Phenylethyl)phosphinic acid, phenylmethyl ester

A mixture of (2-phenylethyl)phosphinic acid (8.5 g., 50 mmole), benzyl bromide (10.26 g., 60 mmole), and anhydrous micropulverized potassium carbonate (13.89 g., 100 mmole) in 20 ml. of dry dimethylformamide is stirred overnight at room temperature in an atmosphere of argon. Some more dimethylformamide (20 ml.) is added and the reaction mixture is heated at 50° overnight. The mixture is diluted with ethyl acetate (250 ml.), filtered, and washed with ethyl acetate (2×50 ml.). The combined extracts are washed with water (2×50 ml.), saturated sodium bicarbonate solution (2×60 ml.), water (2×20 ml.), brine, dried ($Na_2SO_4$), filtered and the solvent stripped to give 12 g. of crude (2-phenylethyl)phosphinic acid, phenylmethyl ester as a colorless oil. Purification by Kugelrohr distillation at a temperature of about 180° and a pressure of 0.15 mm. of Hg gives 6.7 g. of (2-phenylethyl)phosphinic acid, phenylmethyl ester as a colorless oil.

(e) 1-[N-[(2-Phenylethyl)(phenylmethoxy)phosphinyl]-L-alanyl]-L-proline, phenylmethyl ester A mixture of (2-phenylethyl)phosphinic acid, phenylmethyl ester (1.0 g., 3.8 mmole) and 10 ml. of dry benzene is treated with N-chlorosuccinimide (0.6 g.) at 25° in an argon atmosphere. An exotherm is observed. After 30 minutes, the solution is removed from the succinimide via gas tight syringe and the benzene is removed in vacuo. The residue is taken up in 15 ml. of dry tetrahydrofuran and then treated with L-alanyl-L-proline, phenylmethyl ester, hydrochloride salt (1.2 g., 3.8 mmole). A solution of triethylamine (1.7 ml.) in 5 ml. of tetrahydrofuran is added dropwise at 0° (ice bath) under argon. The ice bath is removed and the heterogeneous mixture is stirred for 30 minutes. The reaction mixture is then diluted with ethyl acetate and washed successively with water, saturated sodium bicarbonate solution, 5% potassium bisulfate, saturated sodium bicarbonate, brine, dried ($MgSO_4$), and evaporated. The residue (1.8 g.) is chromatographed on silica gel (75 g.) eluting with ethyl acetate to give 1.2 g. of 1-[N-[(2-phenylethyl)(phenylmethoxy)phosphinyl]-L-alanyl]-L-proline, phenylmethyl ester as an oil. Tlc (ethyl acetate) single spot $R_f$ is 0.2.

(f) 1-[N-[Hydroxy(2-phenylethyl)phosphinyl]-L-alanyl]-L-proline, dilithium salt A mixture of the di(phenylmethyl) ester product from part (e) (1.2 g., 2.2 mmole), triethylamine (1 ml.), water (10 ml.), and methanol (40 ml.) is treated with 10% palladium on carbon catalyst (300 mg.) and shaken on the Parr apparatus at 50 psi for 1.5 hours. The catalyst is removed through a Celite bed and the solvent and excess triethylamine are evaporated. The solid residue is dissolved in 5 ml. of water and applied to an AG-50W-X8 (Li+) column (60 ml. settled volume). The aqueous fractions are filtered (millipore) and lyophilized to give 800 mg. of a white glassy solid. This crude product (450 mg.) is purified on an XAD-2(resin) (200 ml.) column eluting with a linear gradient of water/acetonitrile (0→90% acetonitrile). The acetonitrile and water are stripped, the residue is taken up in water, filtered (millipore) and lyophilized to give 350 mg. of 1-[N-[hydroxy(2-phenylethyl)phosphinyl]-L-alanyl]-L-proline, dilithium salt as a dense white solid.

Anal. calc'd for $C_{16}H_{21},N_2O_5P.2Li.H_2O$ C, 50.02; H, 6.03; N, 7.29; P, 8.06 Found: C, 49.90; H, 5.78; N, 7.29; P, 7.83.

EXAMPLE 4

1-[N-[Hexyl(hydroxy)phosphinyl]-L-alanyl]-L-proline, dilithium salt (a) Hexylphosphinic acid, phenylmethyl ester 1-Hexene (12.5 ml., 0.10 mole) is reacted with sodium hypophosphite monohydrate (15.8 g.; 0.149 mole) in 25 ml. of methanol and treated with 1 ml. of di-t-butylperoxide according to the procedure of Example 1(c) to yield 13.2 g. of hexylphosphinic acid as a colorless oil. Tlc (acetic acid/dichloromethane/methanol; 1:8:1) major spot $R_f0.43$.

Treatment of hexylphosphinic acid (8.0 g., 53.3 mmole), benzylbromide (6.8 ml., 1.2 eq.), and powdered anhydrous potassium carbonate (14.7 g., 2 eq.) in 70 ml. of toluene according to the procedure of Example 1(c) yields 8.0 g. of hexylphosphinic acid, phenylmethyl ester. Tlc (ethyl acetate) shows major spot at $R_f0.6$ (b) 1-[N-[Hexyl(phenylmethoxy)phosphinyl]-L-alanyl]-L-proline, phenylmethyl ester Hexylphosphinic acid, phenylmethyl ester (1.0 g., 4.2 mmole) is treated with L-alanyl-L-proline, phenylmethyl ester, hydrochloride salt (1.3 g., 1.0 eq.) in carbon tetrachloride according to the procedure of Example 1(d) to yield 1.1 g. of 1-[N-[hexyl(phenylmethoxy)phosphinyl]-L-alanyl]-L-proline, phenylmethyl ester. Tlc (ethyl acetate) single spot at $R_f0.4$.

(c) 1-[N-[Hexyl(hydroxyl)phosphinyl]-L-alanyl]-L-proline, dilithium salt

A mixture of the diester product from part (b) (1.1 g., 2.1 mmole), dioxane (30 ml.), water (30 ml.), triethylamine (1 ml.), and 10% palladium-carbon catalyst (250 mg.) is hydrogenated in a Parr apparatus at 50 psi. for five hours. The mixture is filtered through Celite bed and the solvent is stripped. The resulting triethylammonium salt is taken up in water and passed down an AG-50W-X8(Li+) column (60 ml.) eluting with water. The combined aqueous fractions are millipore filtered and lyophilized to obtain a white solid (800 mg.) crude product. The crude product is chromatographed on HP-20(200 ml). column eluting with a linear gradient of water/acetonitrile (0→90%). The pure fractions are combined, concentrated to a small volume, filtered and lyophilized to give 0.14 g. of 1-[N-[hexyl(hydroxy)-phosphinyl]-L-alanyl]-L-proline, dilithium salt. Tlc (isopropanol/conc. NH₄OH/water, 7:2:1) single spot $R_f0.7$.

Anal. calc'd for $C_{14}H_{25}N_2PO_5.2Li.1.1$ mole of $H_2O$; C, 45.94; H, 7.49; N, 7.65; P, 8.5 Found: C, 46.12; H, 7.50; N, 7.20; P, 8.1.

EXAMPLE 5

1-[N-[Hydroxy(octyl)phosphinyl]-L-alanyl]-L-proline, dilithium salt (a) Octylphosphinic acid, phenylmethyl ester 1-Octene (15.7 ml., 0.1 mole) is reacted with sodium hypophosphite monohydrate (15.8 g., 1.5 eq.) and di-t-butylperoxide (1 ml.) in 25 ml. of methanol according to the procedure of Example 1(c) to yield 18 g. of octylphosphinic acid, phenylmethyl ester as a colorless liquid. Tlc (dichloromethane/methanol/acetic acid, 8:1:1) shows major spot at $R_f0.5$.

Reaction of octylphosphonic acid (8 g., 44.9 mmole), benzylbromide (6 ml., 1.2 eq.), and powdered anhydrous potassium carbonate (6.2 g., 2 eq.) in 70 ml. of toluene according to the procedure of Example 1(c) yields 7.7 g. of octylphosphinic acid, phenylmethyl ester as a colorless liquid. Tlc (ethyl acetate) shows a major spot at $R_f0.5$.

(b) 1-[N-[Octyl(phenylmethoxy)phosphinyl]-L-alanyl]-L-proline, phenylmethyl ester Octylphosphinic acid, phenylmethyl ester (1.2 g., 4.5 mmole) is treated with chlorine in $CCl_4$ and the resulting product reacted with L-alanyl-L-proline, phenylmethyl ester, hydrochloride salt (1.4 g.) in tetrahydrofuran according to the procedure of Example 1(d) to yield 1.6 g. of 1-[N-[octyl(phenylmethoxy)phosphinyl]-L-alanyl]-L-proline, phenylmethyl ester as an oil. Tlc (hexane/acetone, 2:1) shows a single spot at $R_f0.3$.

(c) 1-[N-[Hydroxy(octyl)phosphinyl]-L-alanyl]-L-proline, dilithium salt

A mixture of the diester product from part(b) (1.4 g., 2.6 mmole), dioxane (35 ml.), water (30 ml.), triethylamine (1.1 ml., 3 eq.), and 10% palladium on carbon catalyst (400 mg.) is hydrogenated in a Parr apparatus at 50 psi. for 2 hours. The catalyst is removed by filtration through Celite and the solvent is stripped. The resulting triethyl ammonium salt is taken in water and passed down an AG-50W-X8(Li+) column (60 ml.) eluting with water. The combined aqueous fractions are millipore filtered and lyophilized to give a pale yellow solid (850 mg.) crude product. The crude product is chromatographed on an HP-20 column (200 ml.) eluting with a linear gradient of water/acetonitrile (0→90%). The pure fractions are combined, concentrated to a small volume, filtered, and lyophilized to give 0.35 g. of 1-[N-[hydroxy (octyl)phosphinyl]-L-alanyl]-L-proline dilithium salt as a white solid. Tlc(isopropanol/conc. NH₄OH/water; 7:2:1) shows a single spot at $R_f0.7$.

Anal. calc'd for $C_{16}H_{29}N_2O_5P.2Li.1.5$ mole of $H_2O$: C, 47.88; H, 8.04; N, 6.98; P. 7.7 Found: C, 47.88; H, 7.71; N, 6.83; P, 7.8.

EXAMPLE 6

1-[N-[Hydroxy(phenylmethyl)phosphinyl]-L-alanyl]-L-proline, dilithium salt (a) Phenylmethylphosphonic acid, diethyl ester A mixture of triethylphosphite (6.2 ml., 30 mmole) and benzyl bromide (3.6 ml., 30 mmole) is heated at 130° (bath temperature) under argon for three hours. The mixture is purified by short path distillation to give 5.75 g. of phenylmethylphosphonic acid, diethyl ester as a colorless liquid; b.p. 98°-101° (0.2 mm. of Hg.). Tlc (ethyl acetate) shows a single spot at $R_f$ 0.45.

(b) 1-[N-[Ethoxy(phenylmethyl)phosphinyl]-L-alanyl]-L-proline, phenylmethyl ester A mixture of phenylmethylphosphonic acid diethyl ester (0.92 g., 4.04 mmole) and phosphorus pentachloride (0.85 g., 4.08 mmole) in dry benzene (7 ml.) is refluxed under argon for one hour. The cooled solution is evaporated to dryness at room temperature (0.5 mm. of Hg.), taken up in dry benzene (about 5 ml.) and again evaporated to dryness. The colorless residue is then taken up in dry dichloromethane (10 ml.) and treated with L-alanyl-L-proline, phenylmethyl ester, hydrochloride salt (1.2 g., 3.84 mmole). The resulting suspension is cooled to 0° (ice bath) under argon and treated dropwise with a solution of triethylamine (1.7 ml., 12.3 mmole) in dry dichloromethane (5 ml.) over a period of 15 minutes. After the addition is complete, the ice bath is removed and the mixture is allowed to stir at room temperature for 30 minutes. The mixture is diluted with ethyl acetate, filtered and evaporated to dryness. The residue is taken up in ethyl acetate and washed successively with 5% potassium bisulfate, saturated sodium bicarbonate, saturated sodium chloride, dried ($Na_2SO_4$) and evaporated. The residue is purified by flash chromatography on silica gel (100 g.) eluting with acetone-hexane (2:3) to give 1.56 g. of 1-[N-[ethoxy(phenylmethyl)phosphinyl]-L-alanyl]-L-proline, phenylmethyl ester as a colorless oil. Tlc (ethyl acetate) shows a single spot at $R_f$ 0.16.

(c) 1-[N-[Ethoxy(phenylmethyl)phosphinyl]-L-alanyl]-L-proline

A solution of the ester product from part (b) (1.42 g., 3.1 mmole) in 60 ml. of methanol is treated with 10% palladium-carbon catalyst (350 mg.) and hydrogenated in a Parr apparatus at an initial pressure of 45 psi. for 1.5 hours. The mixture is filtered through Celite and evaporated to dryness to give 1-[N-[ethoxy(phenylmethyl)phosphinyl]-L-alanyl]-L-proline as a colorless foam. Tlc (10% methanoldichloromethane) shows a single spot at $R_f$ 0.31.

(d) 1-[N-[Hydroxy(phenylmethyl)phosphinyl-L-alanyl]-L-proline, dilithium salt

A solution of the product from part (c) (1.12 g., 3.1 mmole) in dry dichlormethane (10 ml.) is treated with bis(trimethylsilyl)acetamide (1.0 ml., 4.04 mmole) and stirred at room temperature under argon for 1.5 hours. The mixture is evaporated to dryness (0.5 mm of Hg.), taken up in dry dichloromethane (8 ml.), treated with bromotrimethylsilane (0.9 ml., 6.82 mmole) and stirred overnight at room temperature under argon. The mixture is again evaporated to dryness (0.5 mm. of Hg.) and the residue treated with a mixture of methanol (8 ml.)—water (2 ml.)—triethylamine (2 ml.) and stirred at room temperature under argon for 30 minutes. The mixture is evaporated to dryness, taken up in water and passed down an AG-50W-X8 ($Li^+$) column (50 ml.) eluting with water. The aqueous fractions containing the product are combined and concentrated to a small volume (about 5 ml.). This solution is applied to an HP-20 column and eluted with a linear gradient of water (100%)—acetonitrile (100%) at a flow rate of 5 ml./min. collecting 5 ml. fractions. The fractions containing the desired material are combined, concentrated to a small volume (about 30 ml.), filtered, and lyophilized to give 0.88 g. of 1-[N-[hydroxy(phenylmethyl)-phosphinyl]-L-alanyl]-L-proline, dilithium salt as a white free flowing powder. Tlc (isopropanol/conc. $NH_4OH$/water; 7:2:1) shows a single spot at $R_f$ 0.5.

Anal. calc'd for $C_{15}H_{19}N_2O_5P.Li.H_2O$: C, 48.66; H, 5.72; N, 7.57; P, 8.37 Found: C, 48.75; H, 5.61; N, 7.71; P, 8.2.

EXAMPLE 7

1-[N-[Hydroxy(phenyl)phosphinyl]-L-alanyl]-L-proline, dilithium salt (a) 1-[N-[Phenylmethoxy(phenylphosphinyl)]-L-alanyl]-L-proline, phenylmethyl ester A mixture of phenylphosphonic dichloride (1.15 ml., 8 mmole) and dry dichloromethane (15 ml.) under argon at 25° is treated dropwise with benzyl alcohol (0.83 ml., 1 eq.) and triethylamine (1.1 ml., 1 eq.) in dichloromethane (5 ml.) over a 20 minute period. A slight exotherm is observed. The reaction mixture is then refluxed for 15 minutes, cooled to 0° (ice bath), and L-alanyl-L-proline, phenylmethyl ester, hydrochloride salt (2.5 g., 1 eq.) is added. The heterogeneous mixture is treated dropwise with triethylamine (2.4 ml., 2.1 eq.) in dichloromethane (8 ml.) over a 5 minute period. The ice bath is removed and the reaction mixture is stirred for an additional 1.5 hours. The solids are removed by filtration and the dichloromethane is stripped from the filtrate. The residue is taken up in ethyl acetate and washed with water, saturated sodium bicarbonate, 5% potassium bisulfate, saturated sodium bicarbonate, brine, dried ($MgSO_4$), and evaporated to give 3.2 g. of residue. The residue is chromatographed on silica gel (110 g.) eluting with ethyl acetate/hexane 3/1 followed by evaporation to yield 1.6 g. of 1-[N-[phenylmethoxy(-phenylphosphinyl)]-L-alanyl]-L-proline, phenylmethyl ester as an oil. Tlc (ethyl acetate) shows a single spot at $R_f$ 0.4. (b) 1-[N-[Hydroxy(phenyl)phosphinyl]-L-alanyl]-L-proline, dilithium salt A mixture of the ester product from part (a) (1.6 g., 3.2 mmole), methanol (50 ml.), water (15 ml.), triethylamine (1.4 ml., 3 eq.), and 10% palladium-carbon catalyst (400 mg.) is hydrogenated in a Parr apparatus at 50 psi. for 1.5 hours. The catalyst is removed by filtration through a Celite bed and the solvent stripped. The resulting triethylammonium salt is taken up in water and run through an AG-50W-X8($Li^+$) column (60 ml.) eluting with water. The combined aqueous fractions are filtered (millipore) and lyophilized to obtain 1 g. of a crude white solid. This crude product is chromatographed on an HP-20(200 ml.) column eluting with a linear gradient of water/acetonitrile (0→90%). The pure fractions are combined, concentrated to a small volume, filtered, and lyophilized to give 650 mg. of 1-[N-[hydroxy(phenyl)phosphinyl]-L-alanyl]-L-proline, dilithium salt. Tlc (isopropanol/conc. NH4OH/water; 7:2:1) shows a single spot at $R_f$ 0.7.

Anal. calc'd for $C_{14}H_{17}N_2O_5P.2Li.1H_2O$: C, 47.21; H, 5.38; N, 7.87; P, 8.7 Found: C, 47.35; H, 5.44; N, 8.03; P, 8.5.

EXAMPLE 8

1-[N-[Hydroxy(3-phenylpropyl)phosphinyl]-L-alanyl]-L-proline, dilithium salt

(a) (3-Phenylpropyl)phosphinic acid, ethyl ester (3-Phenylpropyl)phosphonous acid, diethyl ester (10 g., 41.66 mmole) [prepared as set forth in Example 1 of U.S. Pat. No. 4,168,267] is treated with 40 ml. of water containing concentrated hydrochloric cid (4 drops) according to the procedure of Example 3(b) to yield 8.84 g. of (3-phenylpropyl)phosphinic acid, ethyl ester as a colorless liquid. Tlc (ethyl acetate) shows virtually a single spot at $R_f$ 0.21.

(b) (3-Phenylpropyl)phosphinic acid

The monoester product from part (a) (8.8 g., 41.5 mmole) is treated with 2 N sodium hydroxide (40 ml.) according to the procedure of Example 3(c) to yield 6.9 g. of (3-phenylpropyl)phosphinic acid as a colorless liquid. Tlc (dichloromethane/methanol/acetic acid; 8:1:1) shows virtually a single spot at $R_f$ 0.33.

(c) (3-(Phenylpropyl)phosphinic acid, phenylmethyl ester

A solution of (3-phenylpropyl)phosphinic acid (6.9 g., 37.5 mmole) in toluene-dimethylformamide (60/15) is treated with anhydrous powdered potassium carbonate (10.35 g., 75 mmole) and benzyl bromide (7.7 g., 45 mmole) and the mixture is heated at reflux for 2.5 hours. At this stage, some more benzyl bromide is added and refluxing continued for 1.5 hours more. The reaction mixture is cooled, diluted with ethyl acetate, filtered, and washed with ethyl acetate. The combined ethyl acetate washings are washed successively with water (2×50 ml.), saturated sodium bicarbonate (2×50 ml.), water, brine, dried (Na2SO4), filtered and the solvent removed to give 12 g. of a pale yellow oil. Purification by Kugelrohr distillation at a temperature of 210° and a pressure of 0.15 mm. of Hg. gives 7.2 g. of (3-phenylpropyl)phosphinic acid, phenylmethyl ester as a colorless oil. Tlc (ethyl acetate) shows a single spot at $R_f$ 0.28.

(d) 1-[N-[Hydroxy(3-phenylpropyl)phosphinyl]-L-alanyl]-L-proline, di(phenylmethyl)ester A half saturated solution of dry chlorine in carbon tetrachloride is added dropwise via syringe to a solution of (3-phenylpropyl)phosphinic acid, phenylmethyl ester (2 g., 7.2 mmole) in dry carbon tetrachloride under argon until the yellow color of chlorine persists (9 ml. of half saturated chlorine/carbon tetrachloride). The mixture is evaporated to dryness in vacuo. The colorless residue is taken up in dry tetrahydrofuran (10 ml.), cooled to 0° in ice, and treated with L-alanine-L-proline,phenylmethyl ester, hydrochloride salt (2.25 g., 7.2 mmole). The resulting suspension is treated with a solution of triethylamine (1.8 ml., 18 mmole) in dry tetrahydrofuran (10 ml.) over a 15 minute period. After the addition is complete, the mixture is stirred at 0° for 15 minutes, then allowed to warm to room temperature and stirred for an additional 45 minutes. The mixture is diluted with ethyl acetate, filtered, and evaporated to dryness. The residue is taken up in ethyl acetate (200 ml.), washed successively with 5% potassium bisulfate (2×25 ml.), saturated sodium bicarbonate (2×25 ml.), water, saturated sodium chloride, dried, filtered and the solvent removed to give 3.9 g. of an almost colorless oil. This material is purified by flash chromatography on silica gel (160 g.), elution with dichloromethane:acetone (4:1) to give 2.9 g. of 1-[N-[hydroxy-(3-phenylpropyl)-phosphinyl)-L-alanyl]-L-proline, di(phenylmethyl)ester as a colorless oil. Tlc (acetone/dichloromethane, 1:4) shows $R_f$ at 0.2.

(e) 1-[N-[Hydroxy(3-phenylpropyl)phosphinyl]-L-alanyl]-L-proline, dilithium salt A solution of the diester product from part (d) (1.6 g., 2.9 mmole) in methanol (48 ml.) is treated with water (16 ml.), triethylamine (1.5 ml., 10.8 mmole), and 10% palladium-carbon catalyst and hydrogenated in a Parr apparatus at an initial pressure of 50 psi for 3 hours. The mixture is filtered through Celite, the filter cake is washed with methanol, and the combined filtrate is evaporated to dryness. The residue is taken up in water and applied to an AG-50W-X8(Li+) column (75 ml. settled volume) and eluted with water. Fractions containing the desired product are combined and lyophilized to give 1.2 g. of crude white solid product. This material is purified on an HP-20 column (200 ml. settled volume) eluting with a linear gradient of water (100%)—acetonitrile (100%). Fractions containing the desired product are combined, filtered, and lyophilized to give 500 mg. of 1-[N-[hydroxy(3-phenylpropyl)phosphinyl]-L-alanyl]-L-proline, dilithium salt as a colorless solid. Tlc (isopropanol/conc. NH4OH/water; 7:2:1) shows a single spot at $R_f$ 0.48.

Anal. Calc'd for $C_{17}H_{23}N_2O_5P.2Li.1.5\ H_2O$: C, 50.24; H, 6.44; N, 6.89; P, 7.60. Found: C, 50.24; H, 6.39; N, 6.46; P, 7.5.

EXAMPLE 9

1-[$N^2$-[Hydroxy(4-Phenylbutyl)phosphinyl]-L-lysyl]-L-proline, dilithium salt

(a) $N^2$-[(1,1-Dimethylethoxy)carbonyl]-$N^6$-[(phenylmethoxy)carbonyl]-L-lysine A mixture of $N^6$-[(phenylmethoxy)carbonyl]-L-lysine (5.6 g., 20 mmole) and triethylamine (4.2 ml., 30 mmole) in dioxane (50 ml.)—water (20 ml.) is treated with 2-(t-butoxycarbonyloxyimino)-2-phenylacetonitrile (5.4 g., 21.9 mmole) in dioxane (30 ml.) and stirred at room temperature under argon. The heterogeneous mixture becomes a clear yellow solution after 2 hours. After 4 hours, the mixture is diluted with water and extracted with ethyl acetate (100 ml.) and then with ethyl acetate (50 ml.)-ether (40 ml.). The aqueous layer is acidified with 5% citric acid to pH4 and extracted twice with ethyl acetate (2×80 ml.). The combined extracts are washed successively with water (2×50 ml.), brine, dried (Na2SO4), and the solvent stripped to give 7.5 g. of $N^2$-[(1,1-dimethylethoxy)carbonyl]-$N^6$-[(phenylmethoxy)carbonyl]-L-lysine as a colorless oil. Tlc (dichloromethane/methanol, 5:1) shows a single spot at $R_f$ 0.32.

(b)
1-[$N^2$-[(1,1-Dimethylethoxy)carbonyl]-$N^6$-[(phenylmethoxy)carbonyl]-L-lysyl]-L-proline, phenylmethyl ester A solution of the product from part (a) (7 g., 18.4 mmole) in dry chloroform (35 ml.) cooled to −15° is treated with N-methyl morpholine (2.06 ml.) and isobutyl chloroformate (2.52 ml., 18.4 mmole) and stirred in an atmosphere of argon for 15 minutes. A white precipitate gradually forms. L-Proline, phenylmethyl ester hydrochloride salt (4.446 g., 18.4 mmole) is added followed by N-methyl morpholine (2.06 ml.). The resulting mixture is stirred at −15° for one hour, allowed to warm to room temperature, and stirred overnight. The reaction mixture is diluted with ethyl acetate (200 ml.), filtered and evaporated to dryness. The residue is taken up in ethyl acetate (200 ml.), washed successively with water, 5% potassium bisulfate (2×100 ml.), water, brine, dried ($Na_2SO_4$), and the solvent removed to give 12 g. of a pale yellow oil. This material is purified by flash chromatography on silica gel (350 g.) eluting with ethyl acetate-hexane (1:1) to give 7.4 g. of 1-[$N^2$-[(1,1-dimethylethoxy)carbonyl]-$N^6$-[(phenylmethoxy)carbonyl]-L-lysyl]-L-proline, phenylmethyl ester as a colorless oil. Tlc (ethyl acetate-hexane, 1:1) shows a single spot at $R_f$ 0.2.

(c)
1-[$N^6$-[(Phenylmethoxy)carbonyl]-L-lysyl]-L-proline, phenylmethyl ester, hydrochloride salt A solution of the peptide product from part (b) (7 g., 12.3 mmole) in distilled trifluoroacetic acid (20 ml.) is stirred at room temperature under argon for 30 minutes. The excess trifluoroacetic acid is removed in vacuo (0.15 mm. of Hg.). The crude trifluoroacetate salt (7.2 g.) is dissolved in dry ethyl acetate (5 ml.) and treated with a saturated solution of dry hydrochloric acid in ethyl acetate (50 ml.). Ethyl acetate is decanted from the separated oil and the residue is triturated with ethyl acetate. The residue is dried in vacuo (0.15 mm. of Hg.) for two hours to give 4.9 g. of 1-[$N^6$-[(phenylmethoxy)carbonyl]-L-lysyl]-L-proline, phenylmethyl ester, hydrochloride salt as a colorless hygroscopic foam.

Anal. calc'd for $C_{26}H_{34}O_5N_3Cl.0.7 H_2O$: C, 60.44; H, 6.91; N, 8.13; Cl, 6.86 Found: C, 60.41; H, 6.93; N, 8.01; Cl, 6.91.

(d)
1-[$N^2$-[(4-Phenylbutyl)(phenylmethoxy)phosphinyl]-$N^6$-[(phenylmethoxy)carbonyl]-L-lysyl]-L-proline, phenylmethyl ester A half saturated solution of dry chlorine in carbon tetrachloride is added dropwise by syringe to a solution of (4-phenylbutyl)phosphinic acid, phenylmethyl ester (1.0 g., 3.47 mmole), from Example 1 (c), in 5 ml. of dry carbon tetrachloride under argon until the yellow color of excess chlorine persists. The mixture is evaporated to dryness (0.15 mm. of Hg), and the residue is taken up in 5 ml. of dry tetrahydrofuran and treated with 1-[$N^6$-[(phenylmethoxy)carbonyl]-L-lysyl]-L-proline, phenylmethyl ester, hydrochloride salt (1.74 g., 3.4 mmole). The resulting suspension is cooled to 0° (ice bath) under argon and treated dropwise with a solution of triethylamine (1.2 ml.) in 6 ml. of dry tetrahydrofuran over a 15 minute period. After the addition is complete, the mixture is stirred at 0° for 15 minutes, then allowed to warm to room temperature and stirred for an additional one hour. The mixture is diluted with ethyl acetate, filtered and evaporated to dryness. The residue is taken up in ethyl acetate, washed successively with 5% potassium bisulfate, water, saturated sodium bicarbonate, saturated sodium chloride, dried ($Na_2SO_4$), and evaporated. The residue (3.2 g.) is purified by flash chromatography on silica gel (120 g.) eluting with dichloromethane-hexane (5:1) to give 1.62 g. of 1-[$N^2$-[(4-phenylbutyl)(phenylmethoxy)phosphinyl]-$N^6$-[(phenylmethoxy)carbonyl]-L-lysyl]-L-proline,phenyl methyl ester as a colorless oil. Tlc (dichloromethane/acetone; 4:1) single spot at $R_f$ 0.42.

(e)
1-[$N^2$-[Hydroxy(4-phenylbutyl)phosphinyl]-L-lysyl]-L-proline, dilithium salt A solution of the ester product from part (d) (1.5 g., 2 mmole) in 36 ml. of methanol is treated with 12 ml. of water, triethylamine (0.9 ml., 6.5 mmole) and 10% palladium-carbon catalyst (0.35 g.) and hydrogenated in a Parr apparatus at an initial pressure of 50 psi. for 3 hours. The mixture is filtered through Celite, the filter cake is washed thoroughly with methanol, and the combined filtrate is evaporated to dryness. The residue is taken up in water and applied to an AG-50W-X8($Li^+$) column (65 ml. settled volume) and eluted with water. Fractions containing the desired material are combined, filtered, and lyophilized to give 840 mg. of the dilithium salt product. This material is purified on a HP-20 column (200 ml. settled volume) eluting with a linear gradient of water-acetonitrile. The desired fractions are combined, filtered and lyophilized to give 450 mg. of 1-[$N^2$-[hydroxy(4-phenylbutyl)phosphinyl]-L-lysyl]-L-proline, dilithium salt as a colorless solid. Tlc (isopropanol/conc. $NH_4OH$/water; 7:2:1) a single spot at $R_f$ 0.24.

Anal. calc'd for $C_{21}H_{32}O_5N_3P.2Li.2.0 H_2O$: C, 51.99; H, 7.48; N, 8.63; P, 6.36 Found: C, 51.99; H, 7.61; N, 8.67; P, 6.4.

EXAMPLE 10

(S)-7-[N-[Hydroxy(4-phenylbutyl)phosphinyl]-L-alanyl]-1,4-dithia-7-azaspiro[4.4]nonane-8-carboxylic acid, dilithium salt

(a) (S)-1,4-Dithia-7-azaspiro[4.4]nonane-8-carboxylic acid, methyl ester, hydrochloride Methanol (100 ml.) is cooled in an ice bath and treated with acetyl chloride (5 ml.) followed by 4,4-[ethylenebis(thio)]-L-proline, hydrochloride salt (9.5 g., 39 mmole). The mixture is stirred at room temperature overnight. The dark brown solution is treated with activated charcoal (8 g.), filtered through Celite and evaporated to give after trituration with ethyl acetate, a yellow-brown solid. This is recrystallized from methanol-ether (2:3) to give 6.65 g. of (S)-1,4-dithia-7-azaspiro[4.4]nonane-8-carboxylic acid, methyl ester, hydrochloride as a pale yellow solid, m.p. 158°–161°. Tlc (dichloromethane/methanol/acetic acid; 8:1:1) shows a single spot at $R_f$ 0.57.

(b)
(S)-7-[N-[(1,1-Dimethylethoxy)carbonyl]-L-alanyl]-1,4-dithia-7-azaspiro[4.4]nonane-8-carboxylic acid, methyl ester A solution of N-[(1,1-dimethylethoxy)-carbonyl]-L-alanine (2.48 g., 13.1 mmole) in dry chloroform (25 ml.) at −15° is treated with N-methyl morpholine (1.47 ml., 13.1 mmole) followed by isobutyl chloroformate (1.8 ml., 13.1 mmole). After 25 minutes, (S)-1,4-dithia-7-azaspiro[4.4]nonane-8-carboxylic acid, methyl ester, hydrochloride (3.35 g., 13.1 mmole) and N-methyl morpholine (1.47 ml., 13.1 mmole) are added; gas evolution is observed. The mixture is kept below −10° for one hour, then allowed to warm to room temperature, and stirred overnight under argon. The mixture is diluted with ethyl acetate, filtered, and the filtrate is evaporated to dryness. The residue is taken up in ethyl acetate, washed successively with 5% potassium bisulfate, saturated sodium bicarbonate, saturated sodium chloride, dried ($Na_2SO_4$), filtered, and evaporated. The residue (5.6 g.) is purified by flash chromatography on silica gel (200 g.) eluting with ethyl acetate-hexane (1:2) to give 4.5 g. of (S)-7-[N-[(1,1-dimethylethoxy)carbonyl]-L-alanyl]-1,4-dithia-7-azaspiro[4.4]nonane-8-carboxylic acid, methyl ester as a colorless foam. Tlc (ethyl acetate/hexane; 1:1) shows a single spot at $R_f$ 0.28.

(c)
(S)-7-(L-Alanyl)-1,4-dithia-7-azaspiro[4.4]nonane-8-carboxylic acid, methyl ester, hydrochloride salt A solution of the product from part (b) (4.5 g., 11.5 mmole) in distilled trifluoroacetic acid (15 ml.) is stirred at room temperature under argon for 30 minutes. Excess trifluoroacetic acid is removed in vacuo (0.15 mm. of Hg.) for 2 hours to give 4.6 g. of colorless oil. This oil is dissolved in ethyl acetate (5 ml.) and treated with a saturated solution of dry hydrochloric acid in ethyl acetate (30 ml.). The resulting precipitate is collected and washed with ethyl acetate to give 3.2 g. of (S)-7-(L-alanyl)-1,4-dithia-7-azaspiro[4.4]-nonane-8-carboxylic acid, methyl ester, hydrochloride salt as a colorless crystalline solid, m.p. 205°–206°. Tlc (dichloromethane/methanol/acetic acid; 8:1:1) shows a single spot at $R_f$ 0.44.

(d)
(S)-7-[N-[Ethoxy(4-phenylbutyl)phosphinyl]-L-alanyl]-1,4-dithia-7-azaspiro[4.4]nonane-8-carboxylic acid, methyl ester A half saturated solution of dry chlorine in carbon tetrachloride is added dropwise by syringe to a solution of (4-phenylbutyl)phosphinic acid, phenylmethyl ester (1.9 g., 8.4 mmole), from Example 1(c), in 6 ml. of dry carbon tetrachloride under argon until the yellow color of excess chlorine persists. The mixture is evaporated to dryness (0.15 mm. of Hg.), and the colorless residue is taken up in 12 ml. of dry tetrahydrofuran and treated with (S)-7-(L-alanyl)-1,4-dithia-7-azaspiro[4.4]nonane-8-carboxylic acid, methyl ester, hydrochloride salt (2.74 g., 8.4 mmole). The resulting suspension is cooled to 0° (ice bath) under argon and treated dropwise with a solution of triethylamine (2.7 ml.) in 12 ml. of dry tetrahydrofuran over a 15 minute period. After the addition is complete, the mixture is stirred at 0° for 15 minutes, then allowed to warm to room temperature and stirred for an additional 45 minutes. The mixture is diluted with ethyl acetate, filtered and evaporated to dryness. The residue is taken up in ethyl acetate, washed successively with 5% potassium bisulfate, saturated sodium bicarbonate, saturated sodium chloride, dried ($Na_2SO_4$), and evaporated. The residue (4 g.) is purified by flash chromatography on silica gel (140 g.) eluting with hexane-acetone (5:3) to give 2.7 g. of (S)-7-[N-[ethoxy(4-phenylbutyl)phosphinyl]-L-alanyl]-1,4-dithia-7-azaspiro[4.4]nonane-8-carboxylic acid, methyl ester as a colorless oil. Tlc (dichloromethane/acetone; 3:2) shows a single spot at $R_f$ 0.48.

(e)
(S)-7-[N-[Ethoxy(4-phenylbutyl)phosphinyl]-L-alanyl]-1,4-dithia-7-azaspiro[4.4]nonane-8-carboxylic acid A solution of the methyl ester product from part (d) (1.5 g., 2.9 mmole) in dioxane (4 ml.) is treated with 9 ml. of lithium hydroxide solution (0.96 N) and stirred in an atmosphere of argon at room temperature for 30 minutes. The reaction mixture is diluted with water and washed with ethyl acetate. The aqueous layer is acidified to pH 4 by the addition of 10% citric acid and the separated oil is extracted with ethyl acetate (2×150 ml.). The organic layer is washed with water, brine, dried ($Na_2SO_4$) filtered and the solvent removed to give 1.46 g. of (S)-7-[N-[ethoxy(4-phenylbutyl)phosphinyl]-L-alanyl]-1,4-dithia-7-azaspiro[4.4]nonane-8-carboxylic acid. Tlc (dichloromethane/methanol; 5:1) shows a single spot at $R_f$ 0.32.

(f)
(S)-7-[N-[Hydroxy(4-phenylbutyl)phosphinyl]-L-alanyl]-1,4-dithia-7-azaspiro[4.4]nonane-8-carboxylic acid, dilithium salt A solution of the monoacid product from part (e) (1.4 g., 2.8 mmole) in dry dichloromethane (10 ml.) is treated with bis(trimethylsilyl)acetamide (1 ml., 4 mmole) and stirred at room temperature under argon for 1.5 hours. The mixture is evaporated to dryness (0.15 mm. of Hg.), taken up in dry dichloromethane (15 ml.), treated with bromotrimethylsilane (0.9 ml., 6.8 mmole) and stirred overnight at room temperature under argon. The mixture is again evaporated to dryness (0.15 mm. of Hg.) and the residue treated with a mixture of methanol (8 ml.)—water (2 ml.)—triethylamine (4 ml.) and stirred at room temperature under argon for 30 minutes. The mixture is evaporated to dryness, taken up in water and passed through an AG-50W-X8($Li^+$) column (50 ml.) eluting with water. Fractions containing the dilithium salt product are combined and lyophilized to give 1.4 g. of crude white solid. This material is purified on an HP-20 column (200 ml. bed volume) eluting with a linear gradient of water (100%)—acetonitrile (100%) at a flow rate of 5 ml./min. collected 5 ml. fractions. The fractions containing the desired product are combined, filtered, and lyophilized to give 1 g. of (S)-7-[N-[hydroxy(4-phenylbutyl)phosphinyl]-L-alanyl]-1,4-dithia-7-azaspiro[4.4]nonane-8-carboxylic acid, dilithium salt as a white free flowing powder. Tlc (isopropanol/conc. $NH_4OH$/water; 7:2:1) shows a single spot at $R_f$ 0.41.

Anal. calc'd. for $C_{20}H_{27}O_5N_2S_2P \cdot 2Li \cdot 1.2\ H_2O$: C, 47.57; H, 5.86; N, 5.55; P, 6.1 Found: C, 47.57; H, 5.85; N, 5.83; P, 6.2.

EXAMPLE 11

1-[N-[Hydroxy(4-phenylbutyl)phosphinyl]glycyl]-L-proline, dilithium salt (a)
1-[N-[(1,1-Dimethylethoxy)carbonyl]glycyl]-L-proline, phenylmethyl ester A mixture of N-[(1,1-dimethylethoxy)carbonyl]-glycine (2.5 g., 14.5 mmole), tetrahydrofuran (15 ml.), and carbonyldiimidazole is stirred under argon at 0° (ice bath) for one hour. The resulting imidazolide is then treated with triethylamine (4 ml., 2 eq.) and L-proline, phenylmethyl ester, hydrochloride salt (3.5 g., 1 eq.).

The ice bath is removed and the heterogeneous mixture is stirred for 6 hours. After dilution with ethyl acetate, the mixture is washed with water (twice), saturated sodium bicarbonate; 5% potassium bisulfate (twice), brine, dried (MgSO$_4$), and evaporated. The residue (4.6 g.) is chromatographed on silica gel (80 g.) eluting with ethyl acetate to give 4.3 g. of 1-[N-[(1,1-dimethylethoxy)carbonyl]glycyl]-L-proline, phenylmethyl ester as an oil. Tlc (ethyl acetate) shows a single spot at R$_f$0.8.

(b) 1-Glycyl-L-proline, phenylmethyl ester, hydrochloride salt

A solution of the product from part (a) (4.3 g., 9.9 mmole) and trifluoroacetic acid (8 ml.) is stirred under argon at 25° for 15 minutes. The excess trifluoroacetic acid is evaporated and the residue is treated with saturated hydrochloric acid/ether solution. The resulting oil is washed with ether (twice). Trituration with cold ether (twice) gives an amorphous solid which becomes an oil at room temperature. The residue is dried in vacuo for 72 hours to give 2.9 g. of 1-glycyl-L-proline, phenylmethyl ester, hydrochloride salt as a foam. Tlc (dichloromethane/methanol/acetic acid; 8:1:1) shows a single spot at R$_f$0.5.

Anal. calc'd for C$_{14}$H$_{19}$N$_2$O$_3$Cl.0.75 H$_2$O: C, 53.84; H, 6.62; Cl, 11.35 Found: C, 53.90; H, 6.61; Cl, 11.05

(c)
1-[N-[(4-Phenylbutyl)(phenylmethoxy)phosphinyl]-glycyl]-L-proline phenylmethyl ester (4-Phenylbutyl)phosphinic acid, phenylmethyl ester (1.2 g., 4.2 mmole), from Example 1 (c), in dry chloroform (10 ml.) is treated dropwise with a half saturated solution of dry chlorine in carbon tetrachloride (6 ml.) at 25° in an argon atmosphere. The carbon tetrachloride and excess chlorine are removed in vacuo and the residue is taken up in dry dichloromethane (15 ml.). After the addition of 1-glycyl-L-proline, phenylmethyl ester, hydrochloride salt (1.2 g., 1 eq.), the mixture is treated dropwise with triethylamine (1.8 ml., 3 eq.) in dichloromethane (5 ml.) at 0° (ice bath) and then allowed to warm to room temperature. After stirring for 2 hours, the reaction mixture is diluted with ethyl acetate and then washed with water, saturated sodium bicarbonate, 5% potassium bisulfate (twice), saturated sodium bicarbonate, brine, dried (MgSO$_4$), and evaporated. The residue (2 g.) is chromatographed on silica gel (80 g.) eluting with ethyl acetate to give 1.0 g. of 1-[N-[(4-phenylbutyl)(phenylmethoxy)phosphinyl]glycyl]-L-proline, phenylmethyl ester as an oil. Tlc (ethyl acetate) shows a single spot at R$_f$0.2.

(d)
1-[N-[Hydroxy(4-phenylbutyl)phosphinyl]glycyl]-L-proline, dilithium salt

A mixture of the diester product from part (c) (1.0 g., 1.8 mmole), methanol (50 ml.), water (10 ml.), triethylamine (0.8 ml., 3 eq.) and 10% palladium-carbon catalyst (200 mg.) is hydrogenated in a Parr apparatus at an initial pressure of 50 psi. for 3 hours. The catalyst is removed by filtration through a Celite bed and the solvent stripped. The resulting triethylammonium salt is taken up in water and passed through an AG-50-W-X8(Li$^+$) column (60 ml.). Fractions containing the desired material are combined, filtered, and lyophilized to give 700 mg. of crude product. This material is purified by chromatography on an HP-20 column (200 ml.) eluting with a linear gradient water/acetonitrile (0→90%). The fractions containing the product are combined, concentrated to a small volume, filtered and lyophilized to give 400 mg. of 1-[N-[hydroxy(4-phenylbutyl)phosphinyl]glycyl]-L-proline, dilithium salt as a white solid. Tlc (isopropanol/conc. NH$_4$OH/water; 7:2:1) shows a spot at R$_f$0.7.

Anal. calc'd for C$_{17}$H$_{23}$N$_2$O$_5$P.2Li.2 H$_2$O: C, 49.05; H, 6.54; N, 6.73; P, 7.4 Found: C, 49.10; H, 6.53; N, 6.73; P, 7.3.

EXAMPLE 12

1-[N-[Hydroxy(4-phenylbutyl)phosphinyl]-N-methyl-glycyl]-L-proline, dilithium salt (a)
N-[(1,1-Dimethylethoxy)carbonyl]-N-methylglycine A mixture of sarcosine (1.5 g., 16.7 mmole), triethylamine (3.5 ml., 1 eq.), and water (10 ml.) is treated with 2-(t-butyoxycarbonyloxyimino)-2-phenylacetonitrile (4.5 g., 1.1 eq.) in dioxane (10 ml.) at 25°. After 3 hours, the reaction mixture is diluted with water and then washed twice with ethyl acetate. The aqueous phase is acidified to pH 3.0 with 10% citric acid and the resulting oil is extracted with ethyl acetate (twice). The combined extracts are washed with brine, dried (MgSO$_4$), and evaporated to give 3.0 g. of N-[(1,1-dimethylethoxy)carbonyl]-N-methylglycine as a viscous oil which crystallizes on standing; m.p. 84°-85.5°. Tlc (dichloromethane/methanol/acetic acid; 100:5:5) shows a single spot at R$_f$0.6.

Anal. calc'd for C$_8$H$_{15}$NO$_4$: C, 50.59; H, 7.99; N, 7.40 Found: C, 49.94; H, 7.90; N, 7.25.

(b)
1-[N-[(1,1-Dimethylethoxy)carbonyl]-N-methylglycyl]-L-proline, phenylmethyl ester A mixture of N-[(1,1-dimethylethoxy)carbonyl]-N-methylglycine (2.9 g., 15.3 mmole), dry tetrahydrofuran (15 ml.), and carbonyldiimidazole (2.5 g., 1.0 eq.) is stirred at 0° (ice bath) under argon for 1 hour. The resulting imidazolide is then treated with triethylamine (4.3 ml., 2 eq.) and L-proline, phenylmethyl ester, hydrochloride (3.7 g., 1 eq.). The ice bath is removed and the heterogeneous mixture is stirred under argon for 16 hours. The reaction mixture is taken up in ethyl acetate and washed successively with water (twice), 5% potassium bisulfate (four times), saturated sodium bicarbonate, brine, dried (MgSO$_4$), and evaporated to give a crude reside. The residue is purified by passing through silica (15 g.) eluting with ethyl acetate to give 5.0 g. of 1-[N-[(1,1-dimethylethoxy)carbonyl]-N-methylglycyl]-L-proline, phenylmethyl ester as an oil. Tlc (ethyl acetate) shows a single spot at R$_f$0.8.

(c) 1-(N-Methylglycyl)-L-proline, phenylmethyl ester, hydrochloride salt

The proline ester product from part (b) (5.0 g., 13.3 mmole) is treated with trifluoroacetic acid (5 ml.) at 25° in an argon atmosphere for 1 hour. The trifluoroacetic acid is removed in vacuo and the residue is taken up in ether (15 ml.). The ethereal solution is then treated with a saturated hydrochloric acid/ether solution in small portions to precipitate the hydrochloride salt. The ether is decanted and the remaining oil is triturated with ether (4 times) and then dried in vacuo for 24 hours. The resulting oil is crystallized from toluene-ethyl ether and dried over P$_2$O$_5$ give 4.1 g. of 1-(N-methylglycyl)-L-proline, phenylmethyl ester, hydrochloride salt as a white solid; m.p. 113°–116° (dec.). Tlc (dichloromethane/acetic acid/methanol; 8:1:1) shows a single spot at $R_f$ 0.7.

Anal. calc'd. for $C_{15}H_{21}N_2O_3Cl \cdot 0.5\ H_2O$: C, 55.97; H, 6.89; N, 8.70; Cl, 11.02 Found: C, 56.27; H, 6.69; N, 8.78; Cl, 11.21.

(d)
1-[N-[Ethoxy(4-phenylbutyl)phosphinyl]-N-methylglycyl]-L-proline, phenylmethyl ester A mixture of (4-phenylbutyl)phosphonic acid, diethyl ester (1.7 g., 6.4 mmole), prepared from (4-chlorobutyl)-benzene and triethylphosphite according to the procedure of Example 6(a), benzene (10 ml.), and phosphorus pentachloride (1.3 g., 1 eq.) is refluxed under argon for 30 minutes. The benzene and phosphorus oxychloride are removed in vacuo. The residue is taken up in dry dichloromethane, cooled to 0° (ice bath) under argon and treated with 1-(N-methylglycyl)-L-proline, phenylmethyl ester, hydrochloride salt (2.0 g. 1 eq.). The resulting suspension is treated dropwise with a solution of triethylamine (2.1 ml., 3 eq.) in dichloromethane (5 ml.) over a 5 minute period. The ice-bath is removed and the reaction mixture is allowed to stir for 40 minutes. The reaction mixture is diluted with ethyl acetate and washed successively with water (twice), 5% potassium bisulfate, brine, dried (MgSO$_4$), and evaporated. The residue (3.3 g.) is chromatographed on silica eluting with hexane/acetone (5.3) to give 2.0 g. of 1-[N-[ethoxy(4-phenylbutyl)phosphinyl]-N-methylglycyl]-L-proline, phenylmethyl ester. Tlc (hexane/acetone; 2:1) shows a single spot at $R_f$ 0.2.

(e)
1-[N-[Ethoxy(4-phenylbutyl)phosphinyl]-N-methylglycyl]-L-proline

A mixture of the diester product from part (d) (2.0 g., 4 mmole), 10% palladium-carbon catalyst (350 mg.) and methanol (40 ml.) is hydrogenated in a Parr apparatus at 50 psi. for 1 hour. The catalyst is removed by filtration through a Celite bed and the filtrate evaporated to give 1-[N-[ethoxy(4-phenylbutyl)phosphinyl]-N-methylglycyl]-L-proline as a foam. Tlc (methanol/acetic acid/dichloromethane; 5:5:100) shows a major spot at $R_f$ 0.6.

(f)
1-[N-[Hydroxy(4-phenylbutyl)phosphinyl]-N-methylglycyl]-L-proline, dilithium salt A mixture of the monoester product from part (e) (1.6 g., 4 mmole), dry dichloromethane (8 ml.), and bis(trimethylsilyl)acetamide (1.3 ml., 1.3 eq.) under argon is stirred at 25° for one hour. The dichloromethane and excess bis(trimethylsilyl)acetamide are removed in vacuo and the residue is taken up in dry dichloromethane (8 ml.) and treated with trimethylsilylbromide (1.2 ml., 2 eq.) via gastight syringe. After stirring for 16 hours under argon at 25° the dichloromethane and excess trimethylsilylbromide are removed in vacuo and the residue is taken up in methanol/water/triethylamine (8 ml./2 ml./3 ml.) and stirred under argon at 25° for 15 minutes. The methanol, water and excess triethylamine are removed in vacuo. The resulting triethylammonium salt is taken up in water and run through an AG-50W-X8(Li$^+$) column (60 ml.). The desired fractions are combined, evaporated to a small volume, and chromatographed on an HP-20 (200 ml.) column eluting with a linear gradient of water/acetonitrile (0→90%).

The desired fractions are stripped and the residue taken up in water, filtered, and lyophilized to give 600 mg. of 1-[N-[hydroxy(4-phenylbutyl)phosphinyl]-N-methylglycyl]-L-proline, dilithium salt as a white solid. Tlc (isopropanol/conc. NH$_4$OH/water; 7:2:1) shows a major spot at $R_f$ 0.6.

Anal. calc'd for $C_{18}H_{25}N_2O_5P \cdot 2Li \cdot 1H_2O$: C, 52.43; H, 6.60; N, 6.80; P, 7.5 Found: C, 52.40; H. 6.63; N, 6.92; P, 7.6.

EXAMPLE 13

N-[1-[Hydroxy(4-phenylbutyl)phosphinyl]-L-prolyl]-glycine, dilithium salt (a)
N-[1-[(1,1-Dimethylethoxy)carbonyl]-L-prolyl]-glycine, phenylmethyl ester A mixture of 1-[(1,1-dimethylethoxy)carbonyl]-L-proline (1.7 g., 8 mmole), N-methyl morpholine (0.9 ml., 1 eq.), and dry chloroform (15 ml.) at −20° (CCl$_4$/dry ice bath) under argon is treated with isobutyl chloroformate (1.05 ml.). The mixture is stirred for 20 minutes then treated with N-methyl morpholine (0.9 ml., 1 eq.) and glycine, phenylmethyl ester, 4-toluenesulfonic acid salt (2.7 g., 1 eq.). After stirring for 30 minutes, the cooling bath is removed and the reaction mixture is stirred for 16 hours. The reaction mixture is diluted with ethyl acetate and washed successively with water (twice), 5% potassium bisulfate (twice), saturated sodium bicarbonate, brine, dried (MgSO$_4$), and evaporated to give 2.9 g. of N-[1-[(1,1-dimethylethoxy)carbonyl]-L-prolyl]glycine, phenylmethyl ester as an oil. Tlc (ethyl acetate) shows a single spot at $R_f$ 0.8.

(b) N-(L-Prolyl)glycine, phenylmethyl ester, hydrochloride salt

The product from part (a) (2.3 g., 6.3 mmole) is treated with trifluoroacetic acid (5 ml.) at 25° in an argon atmosphere for 1 hour. The trifluoroacetic acid is removed in vacuo and the residue taken up in ether (15 ml.). The ethereal solution is treated with a saturated hydrochloric acid/ether solution in small portions precipitating the hydrochloride salt. The ether is decanted and the residue is triturated with ether (5 times) then dried in vacuo for 24 hours to give 1.9 g. of N-(L-prolyl)glycine, phenylmethyl ester, hydrochloride salt as a hydroscopic foam. Tlc (dichloromethane/methanol/acetic acid; 8:1:1) shows a single spot at $R_f$ 0.6.

Anal. calc'd for $C_{14}H_{19}N_2O_3Cl \cdot 1.3\ H_2O$: C, 52.07; H, 6.77; N, 8.67; Cl, 10.98 Found: C, 52.06; H, 6.38; N, 8.44; Cl, 10.63.

(c)
N-[1-[Ethoxy(4-phenylbutyl)phosphinyl]-L-prolyl]glycine, phenylmethyl ester

A mixture of (4-phenylbutyl)phosphonic acid, diethyl ester (1.7 g., 6.4 mmole), benzene (10 ml.), and phosphorus pentachloride (1.3 g., 1 eq.) are reflexed under argon for 45 minutes. The benzene and phosphorus oxychloride are removed in vacuo. The residue is taken up in dry dichloromethane (10 ml.), cooled to 0° (ice-bath) and treated with N-(L-prolyl)glycine, phenylmethyl ester, hydrochloride salt (1.9 g., 6.36 mmole). The resulting suspension is treated dropwise with a solution of triethylamine (2.7 ml., 3 eq.) in dichloromethane (5 ml.) under argon. The ice-bath is removed and the heterogeneous mixture is stirred for 1.5 hours. The reaction mixture is diluted with ethyl acetate and washed successively with water (twice), 5% potassium bisulfate, saturated sodium bicarbonate, brine, dried (MgSO₄), and evaporated. The residue (3 g.) is chromatographed on silica (80 g.) eluting with hexane/acetone (5/2) followed by elution with hexane/acetone (2/1) to give 1.65 g. of N-[1-[ethoxy(4-phenylbutyl)phosphinyl]-L-prolyl]glycine, phenylmethyl ester as a yellow oil. Tlc (hexane/acetone; 2:1) shows two spots (isomers at phosphorus) $R_f$ 0.3, 0.4.

(d)
N-[1-[Ethoxy(4-phenylbutyl)phosphinyl]-L-prolyl]glycine

A mixture of the diester product from part (c) (1.65 g., 3.4 mmole), methanol (40 ml.), and 10% palladium-carbon catalyst is hydrogenated in a Parr apparatus for 1.5 hours at 50 psi. The catalyst is removed by filtration through a Celite bed and the methanol stripped to give 1.2 g. of N-[1-[ethoxy(4-phenylbutyl)phosphinyl]-L-prolyl]glycine as an oil. Tlc (methanol/acetic acid/dichloromethane; 5/5/100) major spot at $R_f$ 0.5.

(e)
N-[1-[Hydroxy(4-phenylbutyl)phosphinyl]-L-prolyl]-glycine, dilithium salt

A mixture of the monoester product from part (d) (1.2 g., 3 mmole) in dry dichloromethane (10 ml.) and bis(trimethylsilyl) acetamide (1 ml., 1.3 eq.) is stirred at 25° under argon for 1.5 hours. The dichloromethane and excess bis(trimethylsilyl) acetamide are removed in vacuo. The residue is taken up in dichloromethane (10 ml.) and treated with trimethylsilylbromide (1 ml., 2.2 eq.) via gastight syringe. After stirring for 16 hours at 25° under argon, the dichloromethane and excess trimethylsilylbromide are removed in vacuo. The residue is treated with a mixture of methanol/water/triethylamine (10 ml./2 ml./3 ml.) and stirred at room temperature for 10 minutes. The methanol, water, and excess triethylamine are removed in vacuo and the resulting triethylammonium salt is passed through an AG-50W-X-8(Li⁺) column (60 ml.). The desired fractions are combined, evaporated to a small volume, and chromatographed on an HP-20 column (200 ml.) eluting with a linear gradient of water/acetonitrile (0–90%). The pure fractions are combined and the solvent stripped. The residue is taken up in water, filtered, and lyophilized to give 770 mg. of N-[1-[hydroxy(4-phenylbutyl)phosphinyl]-L-prolyl]glycine, dilithium salt as a white solid. Tlc (isopropanol/conc. NH₄OH/water; 7:2:1) shows a major spot at $R_f$ 0.7.

Anal. calc'd for $C_{17}H_{23}N_2O_5P \cdot 2Li \cdot 1H_2O$: C, 51.26; H, 6.33; N, 7.04; P, 7.8 Found: C, 50.99; H, 6.28; N, 7.01; P, 7.8.

EXAMPLE 14

1-[N-[Hydroxy(methyl)phosphinyl]-L-alanyl]-L-proline, dilithium salt (a) Methyl Phosphonic Acid A mixture of dimethyl methylphosphonate (12.4 g., 0.1 mmole) and 6 N hydrochloric acid (100 ml.) is heated at reflux for 5 hours. Hydrochloric acid is removed under reduced temperature. The residue is treated repeatedly with water (3×50 ml.) and evaporated to give a crystalline solid which is freed from water by azetropic distillation with toluene (2×20 ml.) to give 10.95 g. methyl phosphonic acid; m.p. 89°–91°. (Literature m.p. 94°)

(b) 1-[N-[Hydroxy(methyl)phosphinyl]-L-alanyl L-proline, di(phenylmethyl)ester

Methyl phosphonic acid (480 mg., 5 mmole) is treated with phosphorus pentachloride (2.08 g., 10 mmole). A vigorous reaction takes place and the reaction mixture becomes a liquid. Toluene (2×10 ml.) is added and removed under reduced pressure to remove traces of phosphorus oxychloride. The residue is cooled in ice and treated dropwise with a solution of benzyl alcohol (540 mg., 5 mmole) and triethylamine (505 mg., 5 mmole) in dichloromethane (5 ml.) and stirred at room temperature for 15 minutes. L-Alanine-L-proline, phenylmethyl ester, hydrochloride (1.56 g., 5 mmole) is then added, the mixture is cooled in ice and treated slowly with a solution of triethylamine (1 ml.) in dichloromethane and stirred for one hour at 0° and then at room temperature for one hour. The reaction mixture is diluted with ethyl acetate, filtered and the solvent removed. The residue is once again taken up in ethyl acetate (75 ml.), washed successively with water, 10% potassium bisulfate, saturated sodium bicarbonate, water, brine, dried (Na₂SO₄), filtered and concentrated. The residue (1.25 g.) is purified by flash chromatography on silica gel (45 g.) eluting with acetone-hexane (2:1) to give 840 mg. of 1-[N-[hydroxy(methyl)-phosphinyl]-L-alanyl]-L-proline, di(phenylmethyl)ester as a colorless oil. Tlc (acetone-hexane, 3:1) shows a single spot at $R_f = 0.23$.

(c)
1-[N-[Hydroxy(methyl)phosphinyl]-L-alanyl-L-proline, dilithium salt

A solution of the di(phenylmethyl) ester product from part (b) (1 g., 2.25 mmole) in a mixture of methanol (30 ml.), water (5 ml.) and triethylamine (1.5 ml.) is hydrogenated over 10% palladium-carbon catalyst (300 mg.) in a Parr apparatus at 45 psi for 3.5 hours at room temperature. The mixture is filtered through Celite, the bed is washed thoroughly with methanol and the solvent stripped. The residue is taken up in water and applied to an AG-50-X8 (Li⁺) column resin (40 ml. settled volume) and eluted with water. The desired fractions are combined, filtered and lyophilized to give a colorless solid (600 mg.) which is purified on an HP20 column (200 ml. bed volume) eluting with water. The desired fractions are combined, filtered and lyophilized twice to give 400 mg. of 1-[N-[hydroxy(methyl)phosphinyl]-L-alanyl]-L-proline, dilithium salt as a colorless solid; m.p. >300° (turns pink around 240°). Tlc (isopropanol:NH₄OH:water; 7:2:1) shows a single spot at $R_f = 0.27$.

Anal. calc'd. for $C_9H_{15}O_5PLi_2 \cdot 1.75H_2O$: C, 35.13; H, 6.06; N, 9.1; P, 10.1 Found: C, 35.13; H, 5.99; N, 8.97; P, 9.9.

EXAMPLE 15

1-[N²-[Hexyl(hydroxy)phosphinyl]-L-lysyl]-L-proline, dilithium salt (a) Hexylphosphonic acid, diethyl ester A mixture of n-hexyl bromide (16.5 g., 0.1 mole) and triethyl phosphite (37.4 ml., 0.18 mole) is heated in an oil bath to 158° and distilled to give 14 g. of hexylphosphonic acid, diethyl ester as a colorless liquid, b.p. 75° (0.05 mm.). Tlc (ethyl acetate) shows a single spot at $R_f = 0.39$.

uene/acetone (1:1) to give 1.0 g. of N-[N-[ethoxy(4-phenylbutyl)phosphinyl]-L-alanyl]-N-methylglycine, ethyl ester as an oil after evaporation. Tlc (toluene/acetone; 1:1) shows a single spot at $R_f=0.19$.

(e)
N-[N-[Hydroxy(4-phenylbutyl)phosphinyl]-L-alanyl]-N-methylglycine, dilithium salt A mixture of the diester product from part (d) (1.0 g., 2.4 mmole), trimethylsilylbromide (0.5 ml., 1.5 eq.), and dry dichloromethane (5 ml.) is stirred under argon at room temperature for 16 hours. The dichloromethane and excess trimethylsilylbromide are evaporated in vacuo, the resulting oil is taken up in dry acetonitrile (10 ml.), treated with 1 N lithium hydroxide (6.0 ml., 2.5 eq.) and stirred at room temperature for 2 hours. The acetonitrile is evaporated, the solution is filtered and chromatographed on an HP-20 (200 ml.) column eluting with a linear gradient water-acetonitrile (0→90% acetonitrile). The desired fractions are combined, evaporated to a small volume, filtered, and lyophilized to give 680 mg. of N-[N-[hydroxy(4-phenylbutyl)phosphinyl]-L-alanyl]-N-methylglycine, dilithium salt as a white solid; darkens at 208°. Tlc (isopropanol/conc. $NH_4OH$/water; 7:2:1) shows a single spot at $R_f=0.50$.

Anan. calc'd. for $C_{16}H_{23}N_2O_5PLi_2.2H_2O$ C, 47.60; H, 6.73; N, 6.94; P, 7.7 Found: C, 47.60; H, 6.44; N, 6.96; P, 7.8.

EXAMPLE 17

N-[N-[Hydroxy(4-phenylbutyl)phosphinyl]-L-alanyl]-N-phenylglycine, dilithium salt (a)
N-[N-[(1,1-Dimethylthoxy)carbonyl]-L-alanyl]-N-phenylglycine, ethyl ester A solution of N-[(1,1-dimethylethoxy)carbonyl]-L-alanine (2.48 g., 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-phenylglycine, ethyl ester (2.35 g., 13.1 mmole) is added. The mixture is kept below −10° for one hour, then allowed to warm to room temperature and stirred overnight under argon. The mixture is partitioned between ethyl acetate-5% potassium bisulfate (75 ml. each), and the organic phase is washed successively with 5% potassium bisulfate, saturated sodium bicarbonate, and saturated sodium chloride, dried ($Na_2SO_4$), and evaporated. The residue is purified by flash chromatography on silica gel (85 g.) eluting first with dichloromethane and then ethyl acetate/dichloromethane (1:3) to give 1.72 g. of N-[N-[(1,1-dimethylethoxy)carbonyl]-L-alanyl]-N-phenylglycine, ethyl ester as a colorless oil. Tlc (ethyl acetate-hexane; 1:2) shows a single spot at $R_f=0.43$.

(b) N-(L-Alanyl)-N-phenylglycine, ethyl ester, hydrochloride

N-[N-[(1,1-Dimethylethoxy)carbonyl]-L-alanyl]-N-phenylglycine, ethyl ester (1.7 g., 4.86 mmole) is treated with a saturated solution of hydrochloric acid in ethyl acetate (20 ml., saturated with dry hydrochloric acid at 0°) and stirred at 0° (ice-bath) for 50 minutes. A stream of nitrogen is then passed through the solution to remove excess hydrochloric acid and the solution is evaporated to dryness. The residue is taken up in ethyl acetate (approximately 15 ml.), evaporated again and finally dried in vacuo to give 1.4 g. of N-(L-alanyl)-N-phenylglycine, ethyl ester, hydrochloride as a white foam. Tlc (acetic acid-methanol-dichloromethane; 1:1:8), shows a major spot at $R_f=0.5$, slight impurity (approximately 10%) at $R_f=0.26$.

(c)
N-[N-[Ethoxy(4-phenylbutyl)phosphinyl]-L-alanyl]-N-phenylglycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 50 minutes. The cooled solution is evaporated to dryness at room temperature (0.5 mm of Hg.), taken up in dry benzene (approximately 5 ml.) and evaporated again. The colorless residue is taken up in dry tetrahydrofuran (10 ml.) and treated with the crude N-(L-alanyl)-N-phenylglycine, ethyl ester, hydrochloride (1.2 g., 4.19 mmole). The resulting mixture is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room temperature for one hour, the mixture is partitioned between ethyl acetate-5% potassium bisulfate. The organic phase is washed successively with saturated sodium bicarbonate, saturated sodium chloride, dried ($Na_2SO_4$), and evaporated. The residue (1.76 g.) is purified by flash chromatography on silica gel eluting first with acetone-hexane (1:3) then acetone-hexane (2:3) to give 1.01 g. of N-[N-[ethoxy(4-phenylbutyl)phosphinyl]-L-alanyl]-N-phenylglycine, ethyl ester as a colorless oil. Tlc (acetone-toluene; 1:1) shows a single spot at $R_f=0.35$.

(d)
N-[N-[Hydroxy(4-phenylbutyl)phosphinyl]-L-alanyl]-N-phenylglycine, dilithium salt A solution of the diethyl ester product from part (c) (1.01 g., 2.13 mmole) in dry dichloromethane (3.0 ml.) is treated with trimethylsilylbromide (0.65, 4.93 mmole) and stirred at room temperature under argon for 16 hours. The mixture is then evaporated to dryness (0.5 mm. Hg.) and the residue treated with 1 N lithium hydroxide (6.5 ml., 6.5 mmole) and dioxane (4 ml.) and stirred at room temperature for 1.5 hours. The mixture is concentrated to a small volume taken up in water and filtered. The filtrate is chromatographed on an HP-20 column (200 ml. bed volume) eluting with a linear gradient of water-acetonitrile (0→100% acetonitrile) at a flow rate of 5 ml./min. collecting 5 ml. fractions. Fractions containing the desired product are pooled, evaporated, taken up in water, filtered and lyophilized to give 0.60 g, of N-[N-[hydroxy(4-phenylbutyl)phosphinyl]-L-alanyl]-N-phenylglycine, dilithium salt as a fluffy white solid; m.p.: shrinks at 200°, darkens at 220°, greater than 250°. TLc (isopropanol-conc. $NH_4OH$-water; 7:2:1) shows a single spot at $R_f=0.51$.

Anal. calc'd. for: $C_{21}H_{25}N_2O_5PLi_2.1.35H_2O$: C, 55.47; H, 6.14; N, 6.16; P, 6.81 Found: C, 55.47; H, 5.86; N, 6.20; P, 6.7.

EXAMPLE 18

N-[N-[Hydroxy(4-phenylbutyl)phosphinyl]-L-alanyl]-N-(phenylmethyl)glycine, dilithium salt (a)
N-[N-[(1,1-Dimethylethoxy)carbonyl]-L-alanyl]-N-(phenylmethyl)glycine, ethyl ester A solution of N-[(1,1-dimethylethoxy)carbonyl]-L-alanine (2.48, 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-(phenylmethyl)glycine, ethyl ester (2.53 g., 13.1 mmole) is added. The mixture is kept below −10° for one hour and at room temperature for 1.5 hours. The mixture is partitioned between ethyl acetate-5% potassium bisulfate (75 ml. each), and the organic phase is washed successively with 5% potassium bisulfate, saturated sodium bicarbonate, and saturated sodium chloride, dried ($Na_2SO_4$), and evaporated. The residue is purified by flash chromatography on silica gel (110 g.) eluting first with ethyl acetate-hexane (1:6) then ethyl acetate-hexane (1:3) to give 3.93 g. of N-[N-[(1,1-dimethylethoxy)carbonyl]-L-alanyl]-N-(phenylmethyl)glycine, ethyl ester as a colorless oil. Tlc (ethyl acetate-hexane; 1:2) shows a single spot at $R_f=0.40$.

(b) N-(L-Alanyl)-N-(phenylmethyl)glycine, ethyl ester, hydrochloride

N-[N-[(1,1-Dimethylethoxy)carbonyl]-L-alanyl]-N-(phenylmethyl)glycine, ethyl ester (3.5 g., 9.6 mmole) is treated with a saturated solution of hydrochloric acid in ethyl acetate (30 ml., saturated with dry hydrochloric acid at 0°) and stirred at 0° (ice-bath) for 45 minutes. A stream of nitrogen is then passed through the solution to remove excess hydrochloric acid and the solution is evaporated to dryness. The solid residue is triturated with ethyl ether, collected and dried in vacuo to give 2.62 g. of N-(L-alanyl)-N-(phenylmethyl)glycine, ethyl ester, hydrochloride as a white, slightly hygroscopic solid; m.p. 140°–141°. An analytical sample is recrystallized from acetonitrile-ethyl ether; m.p. 141.5°–142°. Tlc (acetic acid-methanol-dichloromethane; 1:1:8) shows a single spot at $R_f=0.40$.

(c)
N-[N-[Ethoxy(4-phenylbutyl)phosphinyl]-L-alanyl]-N-(phenylmethyl)glycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 45 minutes. The cooled solution is evaporated to dryness at room temperature (0.5 mm. of Hg), taken up in dry benzene (approximately 5 ml.) and evaporated again. The colorless residue is taken up in dry tetrahydrofuran (10 ml.) and treated with N-(L-alanyl)-N-(phenylmethyl)glycine, ethyl ester, hydrochloride (1.2 g., 4.16 mmole). The resulting suspension is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room temperature for one hour, the mixture is partitioned between ethyl acetate-5% potassium bisulfate. The organic phase is washed successively with saturated sodium bicarbonate, saturated sodium chloride, dried ($Na_2SO_4$), and evaporated. The residue is purified by flash chromatography on silica (95 g.) eluting with acetone-hexane (1:2) to give 1.58 g. of N-[N-[ethoxy(4-phenylbutyl)phosphinyl]-L-alanyl]-N-(phenylmethyl)glycine, ethyl ester as a colorless oil. Tlc (acetone-toluene; 1:1) shows a single spot at $R_f=0.43$.

(d)
N-[N-[Hydroxy(4-phenylbutyl)phosphinyl]-L-alanyl]-N-(phenylmethyl)glycine, dilithium salt A solution of the diethyl ester product from part (c) (1.13 g., 2.32 mmole) in dry dichloromethane (3.0 ml.) is treated with trimethylsilylbromide (0.70 ml., 5.3 mmole) and stirred at room temperature under argon for 16 hours. The mixture is then evaporated to dryness (0.5 mm. Hg.) and the residue treated with 1 N lithium hydroxide (7.0 ml., 7.0 mmole) and acetonitrile (5.0 ml.) and stirred at room temperature under argon for 1.5 hours. The mixture is concentrated to a small volume, diluted with water (approximately 5 ml.) and filtered. The filtrate is chromatographed on an HP-20 column (200 ml. bed volume) eluting with a linear gradient of water-acetonitrile (0→100% acetonitrile) at a flow rate of 5 ml./min. collecting 5 ml. fractions. Fractions containing the desired product are pooled, evaporated, taken up in water, filtered and lyophilized to give 0.82 g. of N-[N-[hydroxy(4-phenylbutyl)phosphinyl]-L-alanyl]-N-(phenylmethyl)glycine, dilithium salt as a fluffy white solid; m.p.: gradually darkens above 208°. Tlc (isopropanol-conc. $NH_4OH$-water; 7:2:1) shows a single spot at $R_f=0.58$ Anal. Calc'd. for $C_{22}H_{27}N_2O_5PLi_2.0.5H_2O$: C, 58.29; H, 6.23; N, 6.18; P, 6.83 Found: C, 58.23; H, 6.24; N, 6.28; P, 6.8.

EXAMPLE 19

N-Cyclohexyl-N-[N-[hydroxy(4-phenylbutyl)-phosphinyl]-L-alanyl]glycine, dilithium salt (a) N-(cyclohexyl)glycine, ethyl ester A solution of ethyl bromoacetate (11.1 ml., 0.10 mole) in dry ether (40 ml.) is added dropwise to a solution of cyclohexylamine (11.0 g., 0.11 mole) and triethylamine (17.0 ml., 0.12 mole) in dry ether (80 ml.) at 0° (ice-bath) under argon over a period of 30 minutes. The mixture is then allowed to warm to room temperature and stirred for 16 hours. The mixture is filtered and concentrated. The residue is taken up in dichloromethane, washed with saturated sodium bicarbonate and water, dried ($Na_2SO_4$) and evaporated. The resulting brown liquid (15.5 g.) is purified by short path distillation to give 12.6 g. of N-(cyclohexyl)glycine, ethyl ester as a colorless liquid; b.p. 70°–75° (0.5 mm. of Hg). Tlc (10% methanol-dichloromethane) shows a single spot a $R_f=0.61$ (b)
N-Cyclohexyl-N-[N-(1,1-dimethylethoxy)carbonyl]-L-alanyl]glycine, ethyl ester A solution of N-[(1,1-dimethylethoxy)carbonyl]-L-alanine (2.48, 13.1 mmole) in dry chloroform (20 ml.) at −15° is treated with N-methyl morpholine (1.47 ml., 13.1 mmole) followed by isobutylchloroformate (1.8 ml., 13.1 mmole). After 20 minutes, N-(cyclohexyl)glycine, ethyl ester (2.45 g., 13.2 mmole) is added. The mixture is kept below −10° for one hour, then allowed to warm to room temperature and stirred overnight under argon. The mixture is partitioned between ethyl acetate-5% potassium bisulfate (75 ml. each). The organic phase is washed successively with 5% potassium bisulfate, saturated sodium bicarbonate, and saturated sodium chloride, dried (Na$_2$SO$_4$), and evaporated. The residue (4.6 g.) is purified by flash chromatography on silica gel (110 g.) eluting with ethyl acetate-hexane (1:6) to give 3.70 g. of N-cyclohexyl-N-[N-[(1,1-dimethylethoxy)carbonyl]-L-alanyl]glycine, ethyl ester as a colorless viscous oil. Tlc (ethyl acetate-hexane) shows a single spot at R$_f$=0.45.

(c) N-(L-Alanyl)-N-(cyclohexyl)glycine, ethyl ester, hydrochloride

A solution of N-cyclohexyl-N-[N-[(1,1-dimethylethoxy)carbonyl]-L-alanyl]glycine, ethyl ester (3.65 g., 10.3 mmole) in ethyl acetate (5 ml.) at 0° (ice-bath) is treated with a saturated solution of hydrochloric acid in ethyl acetate (25 ml., saturated with dry hydrochloric acid at 0°) and stirred at 0° (ice-bath) for one hour. A stream of nitrogen is then passed through the solution to remove excess hydrochloric acid and the solution is evaporated to dryness. The residue is taken up in ethyl acetate (approximately 25 ml.) evaporated again and finally dried in vacuo to give 3.0 g. of N-(L-alanyl)-N-(cyclohexyl)glycine, ethyl ester, hydrochloride as a white foam. Tlc (acetic acid-methanol-dichlorimethane; 1:1:8) shows a single spot at R$_f$=0.48.

(d)
N-Cyclohexyl-N-[N-[ethoxy(4-phenylbutyl)phosphinyl]-L-alanyl]glycine, ethyl ester A solution of (4-phenylbutyl)phosphonic acid, diethyl ester (1.08 g., 4.0 mmole) in dry benzene (8 ml.) is treated with phosphorus pentachloride (0.85 g., 4.09 mmole) and refluxed under argon for 45 minutes. The cooled solution is evaporated to dryness at room temperature (0.5 mm of Hg), taken up in dry benzene (approximately 5 ml.) and evaporated again. The colorless residue is taken up in dry tetrahydrofuran (10 ml.) and treated with N-(L-alanyl)-N-(cyclohexyl)glycine, ethyl ester, hydrochloride (1.22 g., 4.17 mmole). The resulting mixture is cooled in an ice-bath and treated dropwise with a solution of triethylamine (1.7 ml., 12.3 mmole) in dry tetrahydrofuran (5 ml.) over a period of 10 minutes. After stirring at 0° for 15 minutes and room remperature for one hour, the mixture is partitioned between ethyl acetate-5% potassium bisulfate. The organic phase is washed successively with saturated sodium bicarbonate, saturated sodium chloride, dried (Na$_2$SO$_4$) and evaporated. The residue is purified by flash chromatography on silica gel (90 g.) eluting with acetone-hexane (1:2) to give 1.82 g. of N-cyclohexyl-N-[N-[ethoxy(4-phenylbutyl)phosphinyl]-L-alanyl]glycine, ethyl ester as a colorless oil. Tlc (acetone-hexane; 1:1) shows a single spot at R$_f$=0.32.

(e)
N-Cyclohexyl-N-[N-[hydroxy(4-phenylbutyl)phosphinyl]-L-alanyl]glycine, dilithium salt A solution of the diethyl ester product from part (d) (1.18 g., 2.46 mmole) in dry dichloromethane (3.0 ml.) is treated with trimethylsilylbromide (0.75 ml., 5.69 mmole) and stirred at room temperature under argon for 16 hours. The mixture is then evaporated to dryness (0.5 mm. Hg) and the residue treated with 1 N lithium hydroxide (10.1 ml., 10.0 mmole) and acetonitrile (8 ml.) and stirred at room temperature for 3 hours. The mixture is concentrated to a small volume, taken up in water and filtered. The filtrate is chromatographed on an HP-20 column (200 ml. bed volume) eluting with a linear gradient of water-acetonitrile (0→100% acetontrile) at a flow rate of 5 ml./min. collecting 5 ml. fractions. Fractions containing the desired product are pooled, evaporated, taken up in water, filtered and lyophilized to give 0.78 g. of N-cyclohexyl-N-[N-[hydroxy(4-phenylbutyl)phosphinyl]-L-alanyl]glycine, dilithium salt as a flurry white solid; m.p.: darkens at 230°, m.p.>280°. Tlc (isopropanol-conc. NH$_4$OH-water; 7:2:1) shows a single spot at R$_f$=0.58.

Anal. calc'd. for C$_{21}$H$_{31}$N$_2$O$_5$PLi$_2$.1.6H$_2$O: C, 54.22; H, 7.41; N, 6.02; P, 6.66 Found: C, 54.22; H, 7.17; N, 5.94; P, 6.7.

EXAMPLES 20–115

Following the procedure of Examples 1 to 19 but employing the phosphonochloridate shown in Col. I and the dipeptide ester shown in Col. II one obtains the diester product shown in Col. III. Both the R$_3$ and R$_6$ ester groups may be removed to yield the corresponding diacid or salt as set forth in Examnples 1(e), 3(f), etc., or only the carboxylic ester group R$_6$ may be removed as set forth in Example 2(d) or in the case of Examples 110–115 only the R$_3$ ester group may be removed.

| Ex. | $R_{21}$ | Col. I $R_3$ | Col. II $R_1$ | Col. II $R_2$ | Col. III X |
|---|---|---|---|---|---|
| 20 | $H_3C-(CH_2)_7-$ | $-CH_2-\phi$ | $-H$ | $-(CH_2)_4NHCOCH_2-\phi$ | piperidine-COOCH$_2\phi$ (L, H) via N-(CH$_2$)$_4$- |
| 21 | $H_3C-$ | $-C_2H_5$ | $-H$ | $-CH_2-\phi$ | piperidine-COOCH$_2\phi$ (L, H) via N-(CH$_2$)$_4$- |
| 22 | $H_5C_2-$ | $-CH(\phi)_2$ | $-C_2H_5$ | $-H$ | piperidine-COOCH$_2\phi$ (L, H) via N-(CH$_2$)$_4$- |
| 23 | $\phi-$ | $-CH_2-\phi$ | cyclopropyl (CH$_2$CH$_2$CH-) | $-H$ | piperidine-COOCH$_2\phi$ (L, H) via N-(CH$_2$)$_4$- |
| 24 | $\phi-(CH_2)_4-$ | $-CH_2-\phi$ | $-H$ | $-(CH_2)_3-NHC(=NH)NH-NO_2$ | piperidine-COOCH$_2\phi$ (L, H) via N-(CH$_2$)$_4$- |
| 25 | $HO-\phi-(CH_2)_3-$ | $-C_2H_5$ | $-H$ | $-CH_3$ | piperidine-COOCH$_2\phi$ (L) via N-CH- |

-continued

| Ex. | Col. I $R_{21}$—P(=O)(OR_3)—Cl, $R_{21}$ | $R_3$ | Col. II HN(R_1)—CH(R_2)—C(=O)—X, $R_1$ | $R_2$ | Col. III $R_{21}$—P(=O)(OR_3)—N(R_1)—CH(R_2)—C(=O)—X, X |
|---|---|---|---|---|---|
| 26 | 4-CH$_3$-C$_6$H$_4$– | –CH$_2$–C$_6$H$_5$ | –H | –(CH$_2$)$_2$–C$_6$H$_5$ | lysine benzyl ester (L), COOCH$_2$C$_6$H$_5$ |
| 27 | 4-CH$_3$O-C$_6$H$_4$-CH$_2$– | –C$_2$H$_5$ | –H | –(CH$_2$)$_4$NHCOCH$_2$-C$_6$H$_5$ | lysine benzyl ester (L), COOCH$_2$C$_6$H$_5$ |
| 28 | 4-F-C$_6$H$_4$-(CH$_2$)$_2$– | –CH$_3$ | –H | –CH$_3$ | lysine benzyl ester (L), COOCH$_2$C$_6$H$_5$ |
| 29 | 2-Cl-cyclohexyl-(CH$_2$)$_4$– | –CH$_2$–C$_6$H$_5$ | –H | –CH$_3$ | lysine benzyl ester (L), COOCH$_2$C$_6$H$_5$ |
| 30 | 4-CH$_3$S-C$_6$H$_4$-CH$_2$– | –C$_2$H$_5$ | –H | –H | lysine t-butyl ester (L), COOC(CH$_3$)$_3$ |
| 31 | C$_6$H$_5$-(CH$_2$)$_4$– | –CH$_2$–C$_6$H$_5$ | –CH$_3$ | –CH$_3$ | lysine benzyl ester (L), COOCH$_2$C$_6$H$_5$ |

-continued
| Ex. | Col. I.<br>$R_{21}-\overset{O}{\underset{OR_3}{P}}-Cl$ | | | Col. II<br>$R_1\ R_2\ O$<br>$HN-CH-C-X$ | | Col. III<br>$O\ R_1\ R_2\ O$<br>$R_{21}-P-N-CH-C-X$<br>$OR_3$ |
|---|---|---|---|---|---|---|
| | $R_{21}$ | $R_3$ | | $R_1$ | $R_2$ | X |
| 32 | 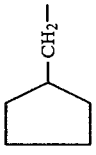 | $-C_2H_5$ | | $-H$ | $-CH_3$ | 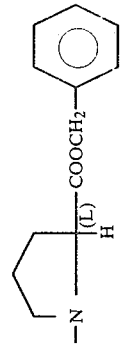 |
| 33 | 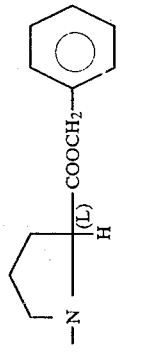 | $-C_2H_5$ | | $-H$ | $-CH_3$ |  |
| 34 | 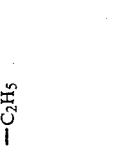 | $-CH_2-$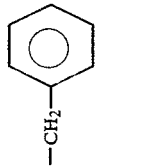 | | $-H$ | $-CH_3$ |  |
| 35 | 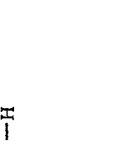 | $-CH_2-$ | | $-H$ | $-CF_3$ |  |
| 36 |  | $-C_2H_5$ | | $-H$ | $-CH_3$ |  |
| 37 | 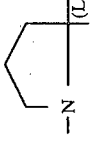 | $-C_2H_5$ | | $-H$ | $-CH_3$ | 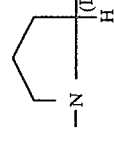 |

-continued

| Ex. | Col. I<br>$R_{21}$—P(=O)(OR_3)—Cl<br>$R_{21}$ | $R_3$ | Col. II<br>$R_1$R_2$—CH—C(=O)—X$<br>HN—<br>$R_1$ | $R_2$ | Col. III<br>$R_{21}$—P(=O)(OR_3)—N(R_1)—CH(R_2)—C(=O)—X<br>X |
|---|---|---|---|---|---|
| 38 | 3-pyridyl-CH$_2$— | —CH$_2$—C$_6$H$_5$ | —H | —CH$_3$ | (L)-N-CH(COOCH$_2$C$_6$H$_5$)-CH$_2$CH$_2$CH$_2$CH$_2$— ring with N |
| 39 | H$_3$C—(CH$_2$)$_6$— | —CH$_2$—C$_6$H$_5$ | —H | —CH$_3$ | N-ring with CH(OH), COOCH$_2$C$_6$H$_5$ (L) |
| 40 | H$_3$C—(CH$_2$)$_3$— | —C$_2$H$_5$ | —H | —CH$_3$ | N-ring with CH(OCH$_3$), COOCH$_2$C$_6$H$_5$ (L) |
| 41 | C$_6$H$_5$— | —C$_2$H$_5$ | —H | —CH$_3$ | N-ring with CH(SCH$_3$), COOC(CH$_3$)$_3$ (L) |
| 42 | C$_6$H$_5$—CH$_2$— | —CH$_3$ | —H | —H | N-ring with CH(Cl), COOCH$_2$C$_6$H$_5$ (L) |

-continued

| Ex. | Col I. $R_{21}$ | $R_3$ | Col II. $R_1$ | $R_2$ | Col III. X |
|---|---|---|---|---|---|
| 43 | -(CH$_2$)$_2$-C$_6$H$_5$ | -CH$_2$-C$_6$H$_5$ | -H | -CH$_3$ | -N(piperidine with F)-CH(L)(H)-COOCH$_2$-C$_6$H$_5$ |
| 44 | -(CH$_2$)$_4$-C$_6$H$_5$ | -C$_2$H$_5$ | -H | -CH$_3$ | -N(piperidine with CH$_3$)-CH(L)(H)-COOCH$_2$-C$_6$H$_5$ |
| 45 | -(CH$_2$)$_6$-C$_6$H$_5$ | -CH$_2$-C$_6$H$_5$ | -H | -CH$_3$ | -N(piperidine with =O)-CH(L)(H)-COOCH$_2$-C$_6$H$_5$ |
| 46 | 3,5-(H$_3$CO)$_2$-C$_6$H$_3$-(CH$_2$)$_4$- | -CH$_2$-C$_6$H$_5$ | -H | -CH$_3$ | -N(piperidine with N$_3$)-CH(L)(H)-COOCH$_2$-C$_6$H$_5$ |
| 47 | 4-Cl-C$_6$H$_4$-(CH$_2$)$_3$- | -CH$_2$-C$_6$H$_5$ | -H | -CH$_3$ | -N(piperidine with N(CH$_3$)$_2$)-CH(L)(H)-COOCH$_2$-C$_6$H$_5$ |

-continued

| | | Col. I. $\begin{array}{c}O\\\parallel\\R_{21}-P-Cl\\\|\\OR_3\end{array}$ | | Col. II $\begin{array}{cc}R_1 & R_2 & O\\ & \| & \|\\HN-CH-C-X\end{array}$ | | Col. III $\begin{array}{cc}O & R_1 & R_2 & O\\\parallel & \| & \| & \|\\R_{21}-P-N-CH-C-X\\\|\\OR_3\end{array}$ |
|---|---|---|---|---|---|---|
| Ex. | $R_{21}$ | $R_3$ | $R_1$ | $R_2$ | | X |
| 48 | H₃C—⌬—(CH₂)₆— | —CH₂—⌬ | —H | —CH₃ | | CH₃C(O)NH—CH(CH₂N—)—CH₂—CH(L)(H)—COOCH₂—⌬ |
| 49 | ⌬_S—CH₂— | —C₂H₅ | —H | —CH₃ | | ⌬CH₂C(O)NH—CH(CH₂N—)—CH(L)(H)—COOCH₂—⌬ |
| 50 | ⌬_O—CH₂— | —C₂H₅ | —H | —CH₃ | | Cyclohexyl—CH(CH₂N—)—CH(L)(H)—COOCH₂—⌬ |
| 51 | ⌬_N—CH₂— | —C₂H₅ | —H | —CH₃ | | ⌬—CH₂—CH(CH₂N—)—CH(L)(H)—COOC(CH₃)₃ |

-continued

| Ex. | R₂₁ | Col. I. $R_{21}-\overset{O}{\underset{OR_3}{P}}-Cl$ R₃ | Col. II $HN-\overset{R_1\ R_2}{\underset{}{C}H}-\overset{O}{\underset{}{C}}-X$ R₁ | R₂ | Col. III $R_{21}-\overset{O}{\underset{OR_3}{P}}-N-\overset{R_1\ R_2}{\underset{}{C}H}-\overset{O}{\underset{}{C}}-X$ X |
|---|---|---|---|---|---|
| 52 | 2-pyridyl-CH₂— | —CH₂-phenyl | —H | —CH₃ | benzyl ester, phenethyl side chain |
| 53 | H₃C— | —CH₂-phenyl | —H | —CH₃ | benzyl ester, 4-fluorobenzyl side chain |
| 54 | H₅C₂— | —CH₂-phenyl | —H | —CH₃ | benzyl ester, thienylmethyl side chain |
| 55 | phenyl-(CH₂)₂— | —CH₂-phenyl | —H | —CH₃ | benzyl ester, furylmethyl side chain |

-continued

| Ex. | R21 | Col. I.<br>$R_{21}-\overset{O}{\underset{OR_3}{P}}-Cl$<br>R3 | Col. II<br>$R_1\ R_2\ O$<br>$HN-CH-C-X$ | | Col. III<br>$R_{21}-\overset{O}{\underset{OR_3}{P}}-N-CH-C-X$ |
|---|---|---|---|---|---|
| | | | R1 | R2 | X |
| 56 | thiophene-CH2– | –CH2–phenyl | –H | –CH3 | [structure with benzyl, COOCH2-phenyl] |
| 57 | furan-CH2– | –CH2–phenyl | –CH3 | –CH3 | [structure with naphthylmethyl, COOCH2-phenyl] |
| 58 | pyridine-CH2– | –CH2–phenyl | –H | –CH3 | [structure with biphenylmethyl, COOCH2-phenyl] |
| 59 | H3C–(CH2)5– | –CH2–phenyl | –H | –H | [structure with OCNH2, COOCH2-phenyl] |

-continued

| Ex. | Col. I $R_{21}$ $\overset{O}{\underset{OR_3}{P}}$ Cl | | $R_3$ | Col. II $R_1 R_2$ $HN-CH-C-X$ $\overset{O}{\|}$ | | Col. III $R_{21}$ $\overset{O}{\underset{OR_3}{P}}$ $N-CH-C-X$ $R_1 R_2$ $\overset{O}{\|}$ |
|---|---|---|---|---|---|---|
| | $R_{21}$ | | | $R_1$ | $R_2$ | X |
| 60 | Ph−(CH$_2$)$_4$− | | −CH$_2$−Ph | −H | −CH$_3$ | [4-F-C$_6$H$_4$-O-CH$_2$-CH(-)-CH$_2$-N, (L)H, COOCH$_2$Ph] |
| 61 | Ph−CH$_2$− | | −CH$_2$−Ph | −H | −(CH$_2$)$_4$NHCOCH$_2$−Ph, O | [Ph-O-CH$_2$-CH(-)-CH$_2$-N, (L)H, COOCH$_2$Ph] |
| 62 | Ph−CH$_2$− | | −C$_2$H$_5$ | −H | −CH$_3$ | [Ph-S-CH$_2$-CH(-)-CH$_2$-N, (L)H, COOC(CH$_3$)$_3$] |
| 63 | Ph−(CH$_2$)$_2$− | | −CH$_2$−Ph | −H | −CH$_3$ | [Ph-S-CH$_2$-CH(-)-CH$_2$-N, (L)H, COOCH$_2$Ph] |

-continued

| Ex. | Col I.<br>$R_{21}-\overset{O}{\underset{OR_3}{P}}-Cl$ | | Col. II<br>$R_1\ R_2\ \ O$<br>$HN-CH-C-X$ | | Col. III<br>$R_1\ R_2\ \ O$<br>$R_{21}-\overset{O}{\underset{OR_3}{P}}-N-CH-C-X$ |
|---|---|---|---|---|---|
| | $R_{21}$ | $R_3$ | $R_1$ | $R_2$ | X |
| 64 | $C_6H_5-(CH_2)_4-$ | $-CH_2C_6H_5$ | $-H$ | $-CH_3$ | 4-F-C$_6$H$_4$-S-CH$_2$-CH(L)(COOCH$_2$C$_6$H$_5$)-N(H)- |
| 65 | $C_6H_5-(CH_2)_4-$ | $-CH_2C_6H_5$ | $-H$ | $-CH_3$ | naphthyl-S-CH$_2$-CH(L)(COOCH$_2$C$_6$H$_5$)-N(H)- |
| 66 | $H_3C-(CH_2)_3-$ | $-CH_2C_6H_5$ | cyclopentyl | $-CH_3$ | biphenyl-S-CH$_2$-CH(L)(COOCH$_2$C$_6$H$_5$)-N(H)- |
| 67 | 4-$H_3$CO-C$_6$H$_4$-(CH$_2$)$_4$- | $-C_2H_4$ | $-H$ | $-CH_3$ | naphthyl-O-CH$_2$-CH(L)(COOCH$_2$C$_6$H$_5$)-N(H)- |

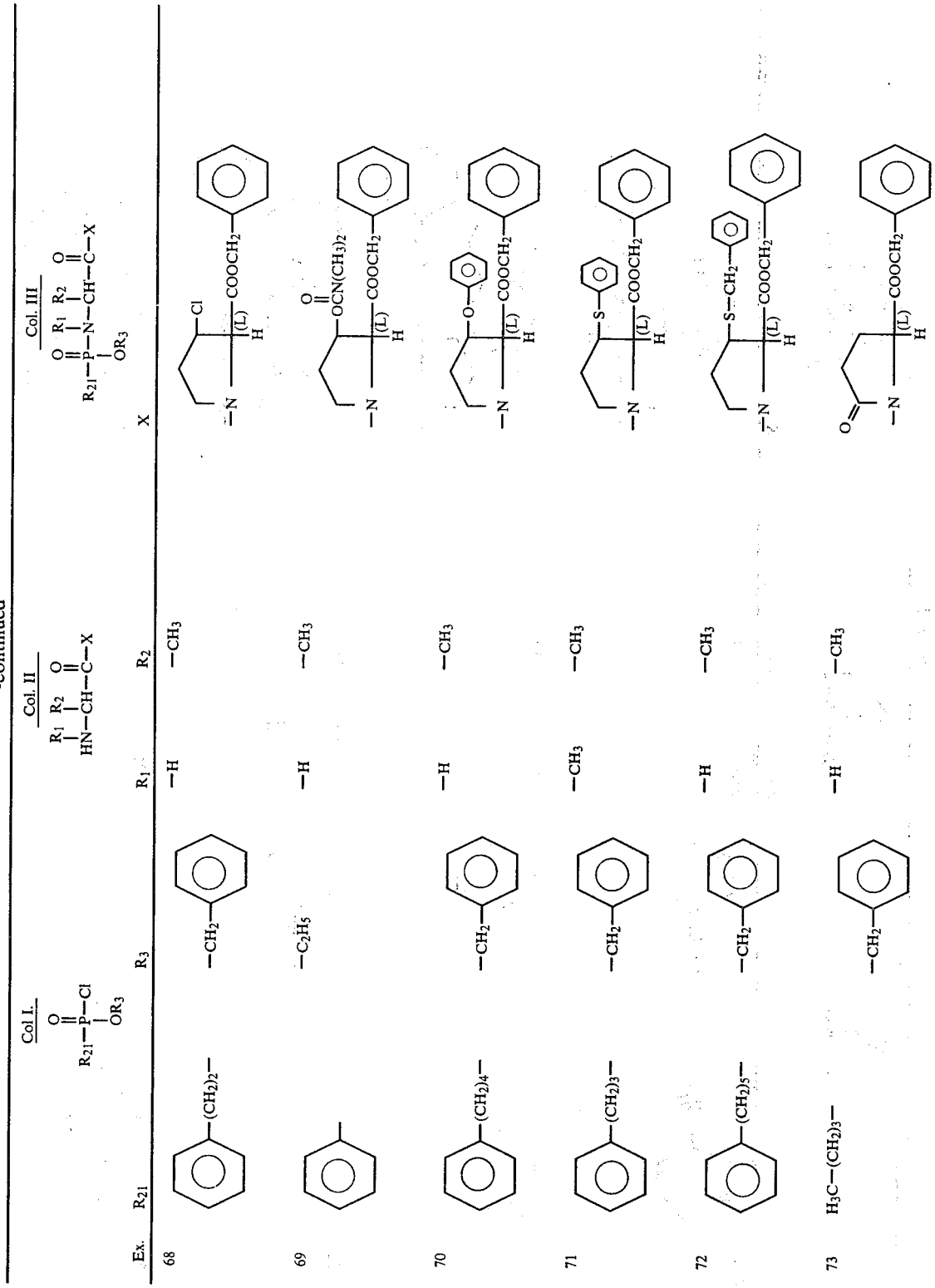

-continued

| Ex. | R₂₁ | Col. I.<br>$\underset{OR_3}{\overset{O}{\underset{\|}{R_{21}-P-Cl}}}$<br>R₃ | Col. II<br>$\underset{HN-CH-C-X}{\overset{R_1\ R_2\ O}{\|\ \|\ \|}}$<br>R₁ | R₂ | Col. III<br>$\underset{R_{21}-P-N-CH-C-X}{\overset{O\ R_1\ R_2\ O}{\|\ \|\ \|\ \|}}$<br>$\underset{OR_3}{}$<br>X |
|---|---|---|---|---|---|
| 74 | Ph-(CH₂)₄- | -CH₂-Ph | -H | -CH₃ | [structure: Ph-CH(Ph)-CH₂-CH₂-N(P)-CH(L)(H)-COOCH₂-Ph] |
| 75 | Ph-(CH₂)₂- | -C₂H₅ | -H | -CH₃ | [structure: 2-HO-C₆H₄-CH(...)-CH₂-CH₂-N-CH(L)(H)-COOCH₂-Ph] |
| 76 | H₃C-(CH₂)₅- | -CH₂-Ph | -H | -CH₃ | [structure: 4-HO-C₆H₄-CH(...)-N-CH(L)(H)-COOCH₂-Ph] |
| 77 | thienyl-CH₂- | -CH₂-Ph | -H | -CH₃ | [structure: CF₂H-CH₂-N-CH(L)(H)-COOCH₂-Ph] |
| 78 | furyl-CH₂- | -CH₂-Ph | -H | -CH₃ | [structure: (H₃CO)(OCH₃)CH-CH₂-N-CH(L)(H)-COOCH₂-Ph] |

-continued

| | Col I. $\underset{R_{21}-\overset{\overset{O}{\|}}{P}-Cl}{OR_3}$ | | | | Col. II $\underset{HN-CH-\overset{\overset{O}{\|}}{C}-X}{R_1\ R_2}$ | | Col. III $\underset{R_{21}-\overset{\overset{O}{\|}}{P}-N-CH-\overset{\overset{O}{\|}}{C}-X}{OR_3\quad\quad\quad\quad}$ |
|---|---|---|---|---|---|---|---|
| Ex. | $R_{21}$ | | $R_3$ | $R_1$ | $R_2$ | | X |
| 83 | H$_3$CS—⟨phenyl⟩—CH$_2$— | | —CH$_2$—⟨phenyl⟩ | —H | —H | | (structure with H$_3$C, CH$_3$, S, S, N, COOCH$_2$—phenyl, (L), H) |
| 84 | ⟨phenyl⟩—(CH$_2$)$_2$— | | —C$_3$H$_7$ | —H | —CH$_3$ | | (structure with N, COOCH$_2$—phenyl, (L), H) |
| 85 | ⟨phenyl⟩—(CH$_2$)$_4$— | | —CH$_2$—⟨phenyl⟩ | —H | —C$_2$H$_5$ | | (structure with S, N, COOCH$_2$—phenyl, (L), H) |
| 86 | ⟨phenyl⟩—(CH$_2$)$_2$— | | —C$_2$H$_5$ | —H | —CH$_3$ | | (structure with CH$_3$, CH$_3$, S, N, COOCH$_2$—phenyl, (L), H) |
| 87 | H$_3$C—(CH$_2$)$_5$— | | —CH$_2$—⟨phenyl⟩ | —H | —CH$_3$ | | (structure with S, phenyl, N, COOCH$_2$—phenyl, (L), H) |

-continued

| Ex. | Col. I.<br>$\begin{array}{c}O\\\parallel\\R_{21}-P-Cl\\\mid\\OR_3\end{array}$ | | | Col. II<br>$\begin{array}{cc}R_1 & R_2 & O\\\mid & \mid & \parallel\\HN-CH-C-X\end{array}$ | | Col. III<br>$\begin{array}{cc}O & R_1 & R_2 & O\\\parallel & \mid & \mid & \parallel\\R_{21}-P-N-CH-C-X\\\mid\\OR_3\end{array}$ |
|---|---|---|---|---|---|---|
| | $R_{21}$ | $R_3$ | | $R_1$ | $R_2$ | X |
| 88 | Ph—(CH$_2$)$_4$— | —CH$_2$—Ph | | —H | —CH$_3$ | —NH—CH$_2$—COOCH$_2$—Ph |
| 89 | Ph—(CH$_2$)$_2$— | —CH$_2$—Ph | | —H | —CH$_3$ | —NH—CH(L)—COOCH$_2$—Ph, CH$_2$CH(CH$_3$)$_2$ side chain |
| 90 | Ph— | —CH$_2$—Ph | | —H | —CH$_3$ | —N(CH$_3$)—CH$_2$—COOCH$_2$—Ph |
| 91 | Ph—(CH$_2$)$_2$— | —C$_2$H$_5$ | | —H | —CH$_3$ | —N(cyclopentyl)—CH$_2$—COOCH$_2$—Ph |
| 92 | Ph—(CH$_2$)$_4$— | —CH$_2$—Ph | | —H | —CH$_3$ | —N(CH$_2$Ph)—CH$_2$—COOCH$_2$—Ph |

-continued

| Ex. | R₂₁ <br> Col I. <br> $R_{21}-\overset{\overset{O}{\|}}{P}-Cl$ <br> $\overset{\|}{OR_3}$ | R₃ | R₁ | R₂ <br> Col. II <br> $\overset{R_1\ R_2}{HN-CH}-\overset{\overset{O}{\|}}{C}-X$ | X <br> Col. III <br> $R_{21}-\overset{\overset{O}{\|}}{P}-\overset{R_1\ R_2}{N-CH}-\overset{\overset{O}{\|}}{C}-X$ <br> $\overset{\|}{OR_3}$ |
|---|---|---|---|---|---|
| 93 | H₃C—(CH₂)₅— | —C₂H₅ | —CH₃ | —H | —NH—CH—COOCH₃ (L) <br> $\|$ <br> CH₃ <br> (phenyl) |
| 94 | —(CH₂)₄— phenyl | —C₂H₅ | —H | —CH₃ | —NH—CH—COOCH₂ (L) <br> $\|$ <br> CH₂—phenyl <br> (phenyl) |
| 95 | —(CH₂)₂— phenyl | —CH₂—phenyl | —H | —CH₃ | —NH—CH—COOCH₂—phenyl (L) <br> $\|$ <br> CH₂—(phenyl)—OCH₂—phenyl |

-continued
| Ex. | Col. I $R_{21}-\overset{O}{\underset{OR_3}{P}}-Cl$ | | Col. II $R_1\ R_2\ O$ $HN-CH-C-X$ | | | Col. III $R_{21}-\overset{O}{\underset{OR_3}{P}}-N-\overset{R_1}{\underset{}{C}H}-\overset{R_2}{\underset{}{C}}-\overset{O}{\underset{}{C}}-X$ |
|---|---|---|---|---|---|---|
| | $R_{21}$ | $R_3$ | $R_1$ | $R_2$ | | X |
| 96 | 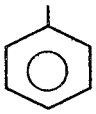 | —$C_2H_5$ | —H | —$CH_3$ | | 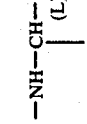 |
| 97 | $H_5C_2$— | —$CH_2$— | —H | —$CH_3$ | |  |
| 98 | 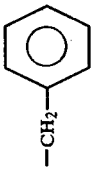 | 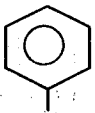—$CH_2$— | —H | —$CH_3$ | |  |

-continued

| Ex. | R₂₁ | Col. I $\underset{OR_3}{\overset{O}{\underset{\|}{R_{21}-P-Cl}}}$ R₃ | R₁ | Col. II $\underset{HN-CH-C-X}{\overset{R_1\ R_2\ \ \ O}{\|\ \|\ \ \ \|}}$ R₂ | Col. III $\underset{R_{21}}{\overset{O}{\underset{\|}{\underset{OR_3}{P}}}}\underset{\|}{\overset{R_1\ R_2\ \ \ O}{N-CH-C-X}}$ X |
|---|---|---|---|---|---|
| 99 | cyclopentyl-CH₂– | –CH₂–phenyl | –H | –CH₃ | –NH–CH(L)–COOCH₂–phenyl, side chain (CH₂)₄–NHCOCH₂–phenyl |
| 100 | (2-thienyl)-CH₂– | –C₂H₅ | –H | –CH₃ | –NH–CH(L)–COOCH₂–phenyl, side chain CH₂–S–CH₂–phenyl |
| 101 | (2-furyl)-CH₂– | –CH₂–phenyl | –H | –CH₃ | –NH–CH(L)–COOCH₂–phenyl, side chain (CH₂)₂–S–CH₃ |
| 102 | phenyl-(CH₂)₂– | –CH₂–phenyl | –H | –CH₃ | –NH–CH(L)–COOCH₂–phenyl, side chain (CH₂)₃–NHC(=NH)–NH–NO₂ |
| 103 | phenyl-(CH₂)₄– | –C₂H₅ | –H | –CH₃ | –NH–CH–COOCH₂–phenyl, side chain CH₂–C(=O)–NH₂ |

| Ex. | Col. I $R_{21}$ | $R_3$ | Col. II $R_1$ | $R_2$ | Col. III X |
|---|---|---|---|---|---|
| 104 | H₃C—(CH₂)₅— | —CH₂—Ph | —H | —CH₃ | —NH—CH(CH₂Ph)(L)—COOCH₂Ph, (CH₂)₂—C(=O)—NH₂ |
| 105 | Ph—(CH₂)₂— | —CH₂—Ph | | —(CH₂)₃— | —NH—CH(CH₃)(L)—COOCH₂Ph |
| 106 | H₃C—(CH₂)₅— | —CH₂—Ph | | —(CH₂)₄— | —NH—CH(CH₂-C₆H₄-OCH₂Ph)(L)—COOCH₂Ph |
| 107 | H₃C—CH₂— | —CH₂—Ph | | —(CH₂)₂— | —NH—CH₂—COOCH₂Ph |
| 108 | Ph—(CH₂)₄— | —CH₂—Ph | | —(CH₂)₃— | —NH—CH(CH₂Ph)(L)—COOCH₂Ph |
| 109 | Ph— | —CH₂—Ph | | —(CH₂)₃— | N-piperidinyl-CH(L)(H)—COOCH₂Ph |

-continued

| Ex. | R₂₁ (Col. I) | R₃ | R₁ (Col. II) | R₂ | Col. III |
|---|---|---|---|---|---|
| 110 | phenyl-(CH₂)₄— | —CH₂—phenyl | —H | —CH₃ | Lys derivative, —O—CH₂—C(CH₃)₃ ester |
| 111 | phenyl-(CH₂)₂— | —CH₂—phenyl | —H | —CH₃ | S,S-bis-thio derivative, —O—CH(CH₃)—CH₃ ester |
| 112 | H₃C—(CH₂)₅— | —CH₂—phenyl | —H | —CH₃ | Lys derivative, —O—benzoyl (phenyl ketone) |
| 113 | phenyl-(CH₂)₂— | —CH₂—phenyl | —H | —CH₃ | S-phenyl derivative, —O—CH₂—C(CH₃)₃ ester |
| 114 | thienyl-CH₂— | —CH₂—phenyl | —H | —CH₃ | naphthyloxy derivative, —O—CH(CH₃)—C₂H₅ ester |

-continued

| Ex. | Col. I R21—P(=O)(OR3)—Cl | R3 | R1 | Col. II R1R2—N(H)—CH—C(=O)—X | R2 | Col. III R21—P(=O)(OR3)—N(R1)—CH(R2)—C(=O)—X |
|---|---|---|---|---|---|---|
| 115 | R21 = Ph(CH2)4— | —CH2—Ph | —H | | —CH3 | X = pyrrolidine-N with 2-(benzoyloxy) substituent |

Reduction of the product of Example 46 yields the corresponding 4-amino product. Similrly, the 4-keto product of Example 45 can be reacted to yield various 4-substituted amino products. The protecting groups shown in Examples 20, 24, 27, 61, 95, 96, 98–100, 102 and 106 are removed following completion of the coupling reaction.

EXAMPLE 116

1-[N-[(6-Aminohexyl)hydroxyphosphinyl]-L-alanyl]-L-proline, dilithium salt

(a) N-(6-Bromohexyl)phthalimide

A mixture of crystalline 6-aminohexanol (11.7 g., 0.1 mole) and phthalic anhydride (14.8 g., 0.1 mole) is heated at 170° for 1.5 hours in an argon atmosphere. The evolved water is then removed with heat and argon flow. The reaction mixture is cooled to 100° and phosphorus tribromide (7.2 ml., 0.086 mole) is added in portions via gas tight syringe to the reaction mixture. A vigorous reaction occurs with each addition. After addition is complete, the reaction mixture is heated at 100° for an additional 30 minutes. The cooled reaction mixture is diluted with ethanol (20 ml.) then poured over ice-water and refrigerated overnight. A yellow solid is filtered and washed several times with cold water until the filtrate is slightly acidic. The crude solid is recrystallized from ethanol to give 21.0 g. of N-(6-bromohexyl)phthalimide as a pale yellow solid; m.p. 54°–55°. Tlc (hexane-ethyl acetate; 1:1) shows a major spot at $R_f=0.8$.

(b) (6-Phthalimidohexyl)phosphonic acid, diethyl ester

A mixture of N-(6-bromohexyl)phthalimide (5.5 g., 17.7 mmole) and triethylphosphite (10.0 ml., 58.4 mmole) is refluxed (bath temperature 160°–165°) under argon for 16 hours. The volatiles are removed by distillation at 100° (bath temperature), 0.5 mm. of Hg to leave a pale yellow viscous oil. The crude product is purified by flash chromatography on silica gel (100 g.) eluting with acetone-hexane (1:2) to give 6.00 g. of (6-phthalimidohexyl)phosphonic acid, diethyl ester as a colorless viscous oil. Tlc (acetone-hexane; 1:1) shows a single spot at $R_f=0.40$.

(c) (6-Phthalimidohexyl)phosphonic acid

A solution of the diethyl ester product from part (b) (4.0 g., 10.9 mmole) in dry dichloromethane (8.0 ml.) is treated with trimethylsilylbromide (3.6 ml., 27.3 mmole) and stirred at room temperature under argon for 22 hours. The mixture is evaporated to dryness (0.5 mm. of Hg) and the residue taken up in dichloromethane (30 ml.)-water (5 ml.) and stirred vigorously for 15 minutes. The organic phase is separated, dried (Na$_2$SO$_4$), and evaporated. The crystalline residue is triturated with ethyl ether to give 3.20 g. of (6-phthalimidohexyl)phosphinic acid as a white solid; m.p., 159°–160°. Tlc (isopropanol-conc. NH$_4$OH-water; 7:2:1) shows a single spot at $R_f=0.20$.

(d) 1-[N-[(Phenylmethoxy)(6-phthalimidohexyl)phosphinyl]-L-alanyl]-L-proline, phenylmethyl ester A suspension of (6-phthalimidohexyl)phosphonic acid (2.34 g., 7.52 mmole) in dry benzene (10 ml.) is treated with phosphorus pentachloride (3.30 g., 15.9 mmole) and stirred at room temperature under argon for 45 minutes. The mixture is then refluxed for 15 minutes, cooled and evaporated to dryness (0.5 mm. Hg). The residue is taken up in dry tetrahydrofuran (10 ml.), cooled in an ice bath and treated dropwise with a solution of benzyl alcohol (0.81 g., 7.5 mmole) and triethylamine (1.05 ml., 7.59 mmole) in dry tetrahydrofuran (5 ml.) over a period of 20 minutes. The mixture is allowed to warm to room temperature, stirred for 30 minutes and then treated with L-alanyl-L-proline, phenylmethyl ester, hydrochloride (2.40 g., 7.68 mmole). The resulting suspension is cooled in an ice-bath and treated dropwise with a solution of triethylamine (4.5 ml.) in tetrahydrofuran (8 ml.). The mixture is warmed to room temperature, stirred for 1.5 hours, diluted with ethyl acetate, filtered and evaporated. The residue is taken up in ethyl acetate and washed successively with 5% potassium bisulfate, saturated sodium bicarbonate, saturated sodium chloride, dried (Na$_2$SO$_4$), and evaporated. The residue is purified by flash chromatography on silica gel (100 g.) eluting with acetone-hexane (1:1) to give 1.75 g. of 1-[N-[phenylmethoxy)(6-phthalimidohexyl)phosphinyl]-L-alanyl]-L-proline, phenylmethyl ester as a colorless glass. Tlc (acetone-toluene; 1:1) shows a single spot at $R_f=0.27$.

(e) 1-[N-[(Phenylmethoxy)[6-[[(phenylmethoxy)carbonyl]amino]hexyl]phosphinyl]-L-alanyl]-L-proline,phenylmethyl ester A solution of 1-[N-[(phenylmethoxy)(6-phthalimidohexyl)phosphinyl]-L-alanyl]-L-proline, phenylmethyl ester (1.50 g., 2.28 mmole) in dioxane (5 ml.) is treated with hydrazine hydrate (0.35 ml., 6.77 mmole) and stirred at room temperature under argon. After 26 hours, the mixture is diluted with toluene and the solvents decanted from the white solid. The solid is triturated with dichloromethane and filtered. The combined filtrate is evaporated to dryness and the residue is taken up in dry tetrahydrofuran (15 ml.). The solution is cooled in an ice bath and treated with triethylamine (0.7 ml., 5.1 mmole) and 95% benzylchloroformate (0.35 ml., 2.3 mmole). The mixture is stirred at 0° for 30 minutes and then partitioned between ethyl acetate-5% potassium bisulfate. The ethyl acetate layer is washed successively with 5% potassium bisulfate, saturated sodium bicarbonate, saturated sodium chloride, dried (Na$_2$SO$_4$), and evaporated. The residue is purified by flash chromatography on silica gel (100 g.) eluting with dichloromethane-acetone (2:1) to give 0.75 g. of 1-[N-[(phenylmethoxy)[6-[[(phenylmethoxy)carbonyl]amino]hexyl]phosphinyl]-L-alanyl]-L-proline, phenylmethyl ester as a colorless glass. Tlc (acetone-toluene; 1:1) shows a single spot at $R_f=0.32$.

(f) 1-[N-[(6-Aminohexyl)hydroxyphosphinyl]-L-alanyl]-L-proline, dilithium salt A solution of the di(phenylmethyl) ester product from part (e) (0.75 g., 1.13 mmole) and triethylamine (1.0 ml., 7.23 mmole) in methanol (30 ml.)-water (10 ml.) is treated with palladium on carbon catalyst (0.35 g.) and hydrogenated in a Parr apparatus at an initial pressure of 50 psi for one hour. The mixture is filtered (Celite) and evaporated to dryness. The residue is taken up in water and applied to an AG-50W-X8(Li+) column (30 ml. bed volume) and eluted with water. The fractions containing the desired product are combined and lyophilized. The crude product is chromatographed on an HP-20 column (200 ml. bed volume)

eluting with water at a flow rate of 5 ml./min. collecting 5 ml. fractions. Fractions containing the desired product are combined, filtered, and lyophilized to give 0.29 g. of 1-[N-[(6-aminohexyl)hydroxyphosphinyl]-L-alanyl]-L-proline, dilithium salt as a white glassy solid; m.p. darkens above 195°. Tlc (isopropanol-conc. NH₄OH-water; 7:2:1) shows a single spot at $R_f=0.23$.

Anal. calc'd. for $C_{14}H_{26}N_3O_5PLi_2.0.3\ H_2O$: C, 45.88; H, 7.32; N, 11.47; P, 8.46 Found: C, 45.88; H, 7.39; N, 11.31; P, 8.5.

EXAMPLES 117–120

Following the procedure of Example 116 but employing the aminoalcohol listed in Col. I one obtains the product listed in Col. II.

| Ex. | Col. I | Col. II |
|---|---|---|
| 117 | 3-aminopropanol | 1-N—[(3-aminopropyl)hydroxyphosphinyl]-L-alanyl]-L-proline, dilithium salt |
| 118 | 2-aminoethanol | 1-N—[(2-aminoethyl)hydroxyphosphinyl]-L-alanyl]-L-proline,dilithium salt |
| 119 | 4-aminobutanol | 1-N—[(4-aminobutyl)hydroxyphosphinyl]-L-alanyl]-L-proline, dilithium salt |
| 120 | 8-aminooctanol | 1-N—[(8-aminooctyl)hydroxyphosphinyl]-L-alanyl]-L-proline, dilithium salt |

Similarly, by employing the various dipeptides of Examples 9–19 and those shown in Col. II of Examples 20–115 within the procedure of Examples 116–120, other compounds within the scope of the invention are obtained.

EXAMPLE 121

1-[N-[[(2,2-Dimethyl-1-oxopropoxy)methoxy]-(4-phenylbutyl)phosphinyl]-L-alanyl]-L-proline, lithium salt (a)

1-[N-[[(2,2-Dimethyl-1-oxopropoxy)methoxy](4-phenylbutyl)phosphinyl]-L-alanyl]-L-proline, phenylmethyl ester A solution of 1-[N-[ethoxy(4-phenylbutyl)phosphinyl]-L-alanyl]-L-proline, phenylmethyl ester from Example 2 (1.35 g., 2.7 mmole) in 10 ml. of dry dichloromethane is treated with bromotrimethylsilane (0.9 ml., 6.8 mmole) and stirred at room temperature under argon for 9.5 hours. The solution is evaporated to dryness (0.2 mm Hg) and the residue taken up in 5 ml. of dioxane and treated with a solution of potassium bicarbonate (550 mg., 5.5 mmole) in 4 ml. of water, stirred at room temperature for 10 minutes and evaporated to dryness. The residue is taken up in water and lyophilized. Tlc (isopropanol/conc. NH₄OH/water, 7:2:1) major spot at $R_f$ is 0.70.

The lyophiliate is suspended in 10 ml. of dry dimethylformamide treated with chloromethylpivalate (0.8 ml., 5.5 mmole) and stirred at room temperature under argon. After 7 hours, additional chloromethylpivalate (0.4 ml.) and anhydrous potassium carbonate (0.3 g.) are added and the resulting mixture is stirred overnight. The mixture is then diluted with ethyl acetate and washed successively with water, 5% potassium bisulfate, saturated sodium bicarbonate, and saturated sodium chloride solution, dried (Na₂SO₄), and evaporated. The residue is purified by flash chromatography on silica gel (100 g.) eluting with acetone/hexane (3:8) to give 1-[N-[[(2,2-dimethyl-1-oxopropoxy)methoxy]-(4-phenylbutyl)phosphinyl]-L-alanyl]-L-proline, phenylmethyl ester as a colorless, viscous oil. Tlc (acetone/dichloromethane, 1:4) single spot at $R_f$ is 0.52.

(b)

1-[N-[[(2,2-Dimethyl-1-oxopropoxy)-methoxy](4-phenylbutyl)phosphinyl]-L-alanyl]-L-proline, lithium salt A solution of the phenylmethyl ester from part (a) (0.52 g., 0.89 mmole) in 30 ml. of ethyl acetate is treated with 10% palladium on carbon catalyst (300 mg.) and hydrogenated in a Parr apparatus at an initial pressure of 48 psi. for 2.5 hours. The mixture is filtered through Celite and evaporated to dryness. The residue is taken up in 5 ml. of dichloromethane treated with triethylamine (0.15 ml., 1.08 mmole) and evaporated to dryness. The resulting triethylammonium salt is taken up in water, applied to an AG-50W-X8 (Li+) column (30 ml. bed volume) and eluted with water. The fractions containing the product are combined, millipore filtered and lyophilized to give 1-[N-[[(2,2-dimethyl-1-oxopropoxy)-methoxy](4-phenylbutyl)phosphinyl]-L-alanyl]-L-proline, lithium salt as a white solid. Tlc (10% methanol/dichloromethane) single spot at $R_f$ is 0.48. 1R (KBr): 1750, 1630 cm⁻¹ (C=O).

Anal. Calc'd. for $C_{24}H_{36}N_2O_7PLi.0.8\ H_2O$: C, 55.77; H, 7.33; N, 5.42; P, 5.99 Found: C, 55.77; H, 7.39; N, 5.43; P, 5.82.

EXAMPLE 122

1-[N-[[(2,2-Dimethyl-1-oxopropoxy)methoxy]-hexylphosphinyl]-L-alanyl]-L-proline, monolithium salt (a)

1-[N-[Ethoxy(hexylphosphinyl)]-L-alanyl]-L-proline, phenylmethyl ester

A solution of hexylphosphonic acid, diethyl ester (2.22 g., 10 mmole) [prepared as set forth in Example 15(a)] in dry benzene (15 ml.) is treated with phosphorus pentachloride (2.2 g., 11 mmole) and refluxed under argon for one hour. The solvent is removed under reduced pressure. Toluene (5 ml.) is added and evaporated to remove traces of phosphorus oxychloride. The residue is dissolved in dichloromethane (20 ml.), treated with L-alanyl-L-proline, phenylmethyl ester, hydrochloride (3.12 g., 10 mmole), cooled in ice and treated dropwise with a solution of triethylamine (3.75 ml.) in dichloromethane (5 ml.) during 10 minutes. The reaction mixture turns slightly rosy after the addition is completed. The reaction mixture is stirred at room temperature for 40 minutes, diluted with ethyl acetate, filtered and the solvent removed. The residue is once again taken up in ethyl acetate (120 ml.), washed successively with water, 10% potassium bisulfate, saturated sodium bicarbonate, water, brine, dried (Na₂SO₄), and evaporated. The residue (4.4 g.) is purified by flash chromatography on silica gel (135 g.) eluting with hexane-acetone (3:2) to give 3.0 g. of 1-[N-[ethoxy(hexylphosphinyl)]-L-alanyl]-L-proline, phenylmethyl ester as a colorless oil. Tlc (ethyl acetate) shows a single spot at $R_f=0.125$.

(b)

1-[N-[[(2,2-Dimethyl-1-oxopropoxy)methoxy]hexyl-phosphinyl]-L-alanyl]-L-proline, phenylmethyl ester A solution of the diester product of part (a) (2.7 g., 6 mmole) in dichloromethane (25 ml.) is treated with trimethylsilylbromide (2 ml.) and stirred at room temperature in an atmosphere of argon. The volatile materials are removed under reduced pressure (0.15 mm. of Hg). The residue is treated with a mixture of methanol (30 ml.), water (5 ml.) and triethylamine (5 ml.) and stirred for 10 minutes. The solvents are removed under reduced pressure to give a triethylammonium salt (3.6 g.) which is converted to the corresponding potassium salt by passing through an AG-50W-X2($K^+$) column (200 ml. bed) and eluting with water. The desired fractions are combined and lyophilized to give 2.63 g. of 1-[N-[hydroxy(hexylphosphinyl)]-L-alanyl]-L-proline, phenylmethyl ester, monopotsssium salt.

A suspension of 2.6 g. of this potassium salt in dry dimethylformamide (35 ml.) and potassium carbonate (1.5 g.) is treated with chloromethylpivalate (1.7 g.) and stirred overnight. Some additional chloromethylpivalate (1 g.) and potassium carbonate (800 mg.) are added and stirring continued for 36 hours. The reaction mixture is diluted with ethyl acetate (200 ml.), washed successively with water (6×50 ml.), 10% potassium bisulfite, saturated sodium bicarbonate, and brine, dried ($Na_2SO_4$), and evaporated. The residue (5 g.) is purified by flash chromatography on silica gel (140 g.) eluting with ethyl acetate to give 1.9 g. of 1-[N-[[(2,2-dimethyl-1-oxopropoxy)methoxy]hexylphosphinyl]-L-alanyl]-L-proline, phenylmethyl ester as a colorless oil. Tlc (dichloromethane-acetone; 4:1) shows a single spot at $R_f$=0.28.

(c)

1-[N-[[(2,2-Dimethyl-1-oxopropoxy)methoxy]hexyl-phosphinyl]-L-alanyl]-L-proline, monolithium salt A solution of the diester product from part (b) (1.19 g., 2 mmole) in ethyl acetate (45 ml.) is treated with 10% palladium on carbon catalyst (500 mg.) and hydrogenated in a Parr apparatus at 45 psi for 3 hours at room temperature. The reaction mixture is filtered (Celite), the bed is washed thoroughly with ethyl acetate and the solvent removed to give 920 mg. of 1-[N-[[(2,2-dimethyl-1-oxopropoxy)methoxy]hexylphosphinyl]-L-alanyl]-L-proline which is dissolved in dichloromethane (5 ml.) containing triethylamine (300 mg.). The solvent is removed and the resulting triethylammonium salt is passed through a column of AG-50W-X8($Li^+$) (50 ml. settled volume) resin eluting with water. The fractions containing the desired product are combined, filtered and lyophilized to give 500 mg. of 1-[N-[[(2,2-dimethyl-1-oxopropoxy)methoxy]hexylphosphinyl]-L-alanyl]-L-proline, monolithium salt as a colorless solid. Tlc (dichloromethane-methanol-acetic acid; 20:1:1) shows a single spot at $R_f$=0.42.

Anal. Calc'd. for $C_{20}H_{36}N_2O_7P \cdot Li$ C, 52.84; H, 7.99; N, 6.16; P, 6.81 Found: C, 52.60; H, 8.25; N, 6.10; P, 6.6.

EXAMPLE 123

1-[N-[[(2,2-Dimethyl-1-oxopropoxy)methoxy]hexyl-phosphinyl]-L-lysyl]-L-proline, monolithium salt (a)

1-[$N^2$-[[(2,2-Dimethyl-1-oxopropoxy)methoxy]hexyl-phosphinyl]-$N^6$-[(phenylmethoxy)carbonyl]-L-lysyl]-L-proline, phenylmethyl ester A solution of 1-[$N^2$-[ethoxy(hexyl)phosphinyl]-$N^6$-[(phenylmethoxy)carbonyl]-L-lysyl]-L-proline, phenylmethyl ester (3.5 g., 5.4 mmole) [prepared as set forth in Example 15(b)] in dry dichloromethane (25 ml.) is treated with trimethylsilylbromide (1.75 ml.) and stirred at room temperature under argon overnight. Volatile materials are removed under vacuum (0.15 mm of Hg), the residue (4.8 g.) is taken up in a mixture of methanol (40 ml.)-water (5 ml.)-triethylamine (5 ml.) and stirred at room temperature for 10 minutes. The solvents are removed in a rotary evaporator and the residue is dissolved in water (5 ml.) and passed through an AG-50W-X2($K^+$) (75 ml. settled volume) column and eluted with water. Fractions containing the desired product are combined, filtered and lyophilized to give 3.74 g. of 1-[$N^2$-[hydroxy(hexyl)phosphinyl]-$N^6$-[(phenylmethoxy)carbonyl]-L-lysyl]-L-proline, phenylmethyl ester, monopotassium salt.

This crude potassium salt (3.74 g.) is suspended in dry dimethylformamide (35 ml.) containing anhydrous potassium carbonate (1.56 g.) and treated with chloromethylpivalate (1.7 ml., 11.3 mmole) and the mixture is stirred at room temperature overnight. Additional chloromethylpivalate (0.85 ml.) and anhydrous potassium carbonate (0.8 g.) are added and the mixture is stirred at room temperature for 48 hours. The reaction mixture is diluted with ethyl acetate (250 ml.), washed successively with water, 10% potassium bisulfate, saturated sodium bicarbonate, water, brine, dried ($Na_2SO_4$), filtered, and evaporated. The residue (3.6 g.) is purified by flash chromatography on silica gel (120 g.) eluting with ethyl acetate to give 1.7 g. of 1-[$N^2$-[[(2,2-dimethyl-1-oxopropoxy)methoxy]hexylphosphinyl]-$N^6$-[(phenylmethoxy)carbonyl]-L-lysyl]-L-proline, phenylmethyl ester as a colorless oil.

(b)

1-[N-[[(2,2-Dimethyl-1-oxopropoxy)methoxy]-hexyl-phosphinyl]-L-lysyl]-L-proline, monolithium salt A mixture of the diester product from part (a) (600 mg., 0.82 mmole), methanol (30 ml.), water (3 ml.), and 10% palladium on carbon catalyst (500 mg.) is hydrogenated in a Parr apparatus at 50 psi for 2.5 hours. The catalyst is removed by filtration (Celite bed) and the solvent evaporated. The residue is taken up in ethyl acetate, treated with triethylamine (0.4 ml., 4.0 eq.) and the excess triethylamine and ethyl acetate are evaporated. The resulting triethylammonium salt is taken up in water and applied to an AG-50W-X8($Li^+$) (10 ml.) column eluting with water. The fractions containing the desired product are combined, evaporated to a small volume and chromatographed on an HP-20 (200 ml.) column eluting with a linear gradient of water-acetonitrile (0→90% acetonitrile). The fractions containing the desired product are combined, evaporated to dryness, taken up in water, filtered, and lyophilized to give 195 mg. of 1-[N-[[(2,2-dimethyl-1-oxopropoxy)methoxy]-hexylphosphinyl]-L-lysyl]-L-proline, monolithium salt as a white solid; m.p. 87°–90°. Tlc (isopropanol-conc.N-H₄OH-water; 7:2:1) shows a single spot at $R_f=0.7$.

Anal. calc'd. for $C_{23}H_{43}N_3O_7PLi \cdot 0.84 H_2O$: C, 52.46; H, 8.55; N, 7.98; P, 5.9 Found: C, 52.46; H, 8.68; N, 7.86; P, 6.0.

EXAMPLES 124–134

Following the procedure of Example 121 but substituting for the chloromethylpivalate the alkylating agents listed below in Col. I, the products listed below in Col. II are obtained.

Similarly, the alkylating agents of Examples 121 to 134 can be employed with ester products of Examples 3 to 109 and 116 to 120 to yield other compounds within the scope of this invention.

EXAMPLE 135

1-[N-[Hydroxy(4-phenylbutyl)phosphinyl]-L-alanyl]-L-proline, disodium salt

Following the procedure of Example 1 but substituting AG-50W-X8 (Na⁺) for the lithium resin in part (e),

| Example | Col. I | Col. II |
|---|---|---|
| 124 | Cl—CH(cyclohexyl)—O—C(=O)—C₂H₅ | 1-[N-[[Cyclohexyl(1-oxopropoxy)methoxy](4-phenylbutyl)phosphinyl]-L-alanyl]-L-proline, lithium salt |
| 125 | Cl—CH(CH(CH₃)₂)—O—C(=O)—C₂H₅ | 1-[N-[[(2-Methyl-1-(1-oxopropoxy)propoxy](4-phenylbutyl)phosphinyl]-L-alanyl]-L-proline, lithium salt |
| 126 | Cl—CH(CH₃)—O—C(=O)—C₂H₅ | 1-[N-[[1-(1-Oxopropoxy)ethoxy](4-phenylbutyl)phosphinyl]-L-alanyl]-L-proline, lithium salt |
| 127 | Cl—CH(CH₃)—O—C(=O)—CH(CH₂CH₃)₂ | 1-[N-[[1-(2-Ethyl-1-oxobutoxy)ethoxy](4-phenylbutyl)phosphinyl]-L-alanyl]-L-proline, lithium salt |
| 128 | Cl—CH(CH(CH₃)₂)—O—C(=O)—(CH₂)₂CH₃ | 1-[N-[[2-Methyl-1-(1-oxobutoxy)propoxy](4-phenylbutyl)phosphinyl]-L-alanyl]-L-proline, lithium salt |
| 129 | Cl—CH(CH(CH₃)₂)—O—C(=O)—(CH₂)₃CH₃ | 1-[N-[[2-Methyl-1-[(1-oxopentyl)oxy]propoxy]-(4-phenylbutyl)phosphinyl]-L-alanyl]-L-proline, lithium salt |
| 130 | Br—CH₂—O—C(=O)—CH₃ | 1-[N-[[(Acetyloxy)methoxy](4-phenylbutyl)phosphinyl]-L-alanyl]-L-proline, lithium salt |
| 131 | Cl—CH₂—O—C(=O)—OC₂H₅ | 1-[N-[[Ethoxycarbonyloxy)methoxy]-(4-phenylbutyl)phosphinyl]-L-alanyl]-L-proline, lithium salt |
| 132 | 3-bromophthalide (Br on isobenzofuranone) | 1-[N-[(1,3-Dihydro-3-oxo-1-isobenzofuranyloxy)(4-phenylbutyl)phosphinyl]-L-alanyl]-L-proline, lithium salt |
| 133 | ClCH₂O—C(=O)—C₆H₅ | 1-[N-[[(Phenylcarbonyloxy)methoxy]-(4-phenylbutyl)phosphinyl]-L-alanyl]-L-proline, lithium salt |
| 134 | Cl—CH(CH₃)—O—C(=O)—CH₃ | 1-[N-[[1-(Acetyloxy)ethoxy](4-phenylbutyl)phosphinyl]-L-alanyl]-L-proline, lithium salt | one obtains 1-[N-[hydroxy(4-phenylbutyl)phosphinyl]-L-alanyl]-L-proline, disodium salt.

This procedure can be employed in Examples 2–134 to give the corresponding mono or disodium salt. Similarly, by employing a potassium resin the corresponding mono or dipotassium salt is obtained.

EXAMPLE 136

1000 tablets each containing the following ingredients:

| | |
|---|---|
| 1-[N—[Hydroxy(4-phenylbutyl)-phosphinyl]-L-alanyl]-L-proline, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the 1-[N-[hydroxy(4-phenylbutyl)phosphinyl]-L-alanyl]-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 134 can be prepared.

EXAMPLE 137

1000 tablets each containing the following ingredients:

| | |
|---|---|
| 1-[N—[[(2,2-Dimethyl-1-oxopropoxy)-methoxy](4-phenylbutyl)phosphinyl]-L-alanyl]-L-proline, sodium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the 1-[N-[[(2,2-dimethyl-1-oxopropoxy)methoxy](4-phenylbutyl)phosphinyl]-L-alanyl]-L-proline, sodium salt, lactose and Avicel and then blending with the corn starch. Magnesium stearate is added and the dry mixture is compressed in a tablet press to form 1000 tablets each containing 50 mg. of active ingredient. The tablets are coated with a solution of Methocel E 15 (methyl cellulose) including as a color a lake containing yellow #6.

In a similar manner, tablets containing 50 mg. of the product of any Examples 1 to 134 can be prepared.

EXAMPLE 138

Two piece #1 gelatin capsules each containing 100 mg. of 1-[N-[ethoxy(4-phenylbutyl)phosphinyl]-L-alanyl]-L-proline, sodium salt are filled with a mixture of the following ingredients:

| | |
|---|---|
| 1-[N—[Ethoxy(4-phenylbutyl)-phosphinyl]-L-alanyl]-L-proline, sodium salt | 100 mg. |

| -continued | |
|---|---|
| Magnesium stearate | 7 mg. |
| Lactose | 193 mg. |
| | 300 mg. |

In a similar manner, capsules containing 100 mg. of the product of any of Examples 1 and 3 to 134 can be prepared.

EXAMPLE 139

An injectable solution is prepared as follows:

| | |
|---|---|
| 1-[N—[Hydroxy(2-phenylethyl)-phosphinyl]-L-alanyl]-L-proline, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1, 2 and 4 to 134.

EXAMPLE 140

1000 tablets each containing the following ingredients:

| | |
|---|---|
| 1-[N—[[(2,2-Dimethyl-1-oxopropoxy)-methoxy](4-phenylbutyl)phosphinyl]-L-alanyl]-L-proline, disodium salt | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the 1-[N-[[2,2-dimethyl-1-oxopropoxy)methoxy](4-phenylbutyl)phosphinyl]-L-alanyl]-L-proline, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any Examples 1 to 120 and 122 to 134.

What is claimed is:

1. A compound of the formula

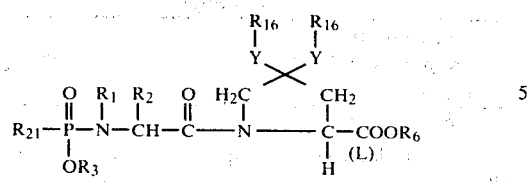

and a pharmaceutically acceptable salt thereof wherein:
Y is oxygen or sulfur and the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent;
$R_1$ is hydrogen, lower alkyl, or cycloalkyl;
$R_2$ is hydrogen, lower alkyl, halo substituted lower alkyl,

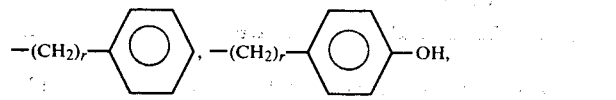

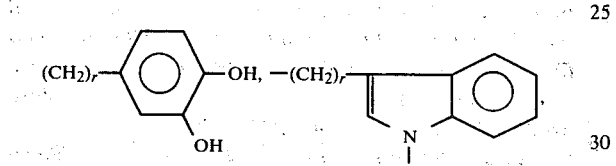

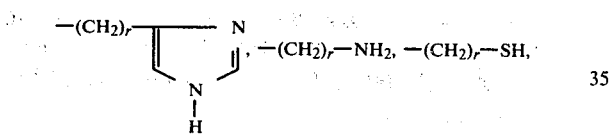

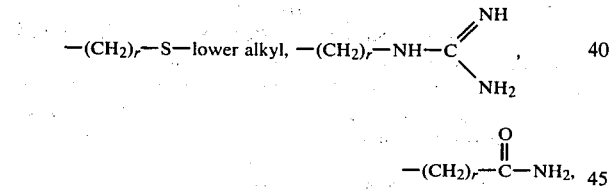

or $R_1$ and $R_2$ taken together are $—(CH_2)_n—$ wherein n is an integer from 2 to 4;
$R_3$ and $R_6$ are independently selected from the group consisting of hydrogen, lower alkyl, benzyl, benzhydryl, and

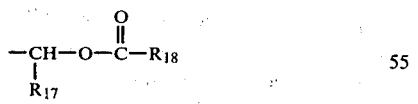

wherein $R_{17}$ is hydrogen, lower alkyl, cycloalkyl, or phenyl, and $R_{18}$ is hydrogen, lower alkyl, lower alkoxy, phenyl or $R_{17}$ and $R_{18}$ taken together are

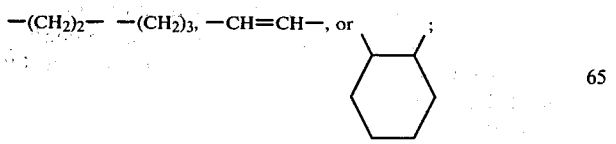

$R_{21}$ is alkyl or 1 to 10 carbons,
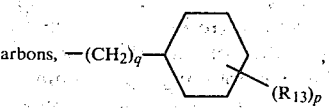

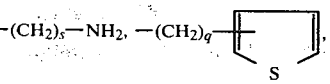

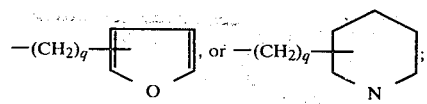

$R_{13}$ is hydrogen, lower alkyl of 1 to 4 carbons, lower alkoxy of 1 to 4 carbons, chloro, bromo, fluoro, trifluoromethyl, hydroxy, phenyl, phenoxy, phenylthio, or phenylmethyl;
r is an integer from 1 to 4;
q is zero or an integer from 1 to 7;
s is an integer from 1 to 8; and
p is one, two or three provided that p is more than one only if $R_{13}$ is hydrogen, methyl, methoxy, chloro, or fluoro.

2. A compound of claim 1 wherein:
Y is oxygen or sulfur and the $R_{16}$ groups join to complete an unsubstituted 5- or 6-membered ring or said ring in which one or more of the carbons has a methyl or dimethyl substituent;
$R_1$ is hydrogen or lower alkyl of 1 to 4 carbons;
$R_2$ is hydrogen, lower alkyl of 1 to 4 carbons, $CF_3$, or amino substituted lower alkyl of 1 to 4 carbons, or $R_1$ and $R_2$ taken together are $—(CH_2)_3—$;
$R_{21}$ is alkyl of 1 to 10 carbons,

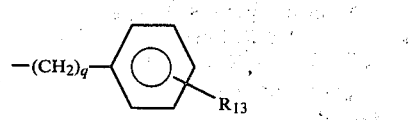

$—(CH_2)_q—$cycloalkyl wherein cycloalkyl is of 5 or 6 carbons,

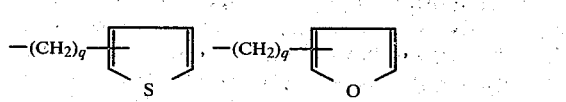

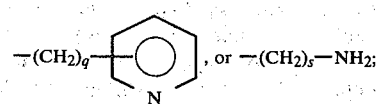

$R_3$ and $R_6$ are independently selected from the group consisting of hydrogen, alkali metal salt, lower alkyl of 1 to 4 carbons, and

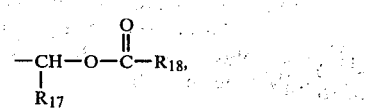

$R_{17}$ is hydrogen, straight or branched chain lower alkyl of 1 to 4 carbons, or cyclohexyl;

$R_{18}$ is straight or branched chain lower alkyl of 1 to 4 carbons or phenyl;

$R_{13}$ is hydrogen, methyl, methoxy, methylthio, chloro, bromo, fluoro, or hydroxy;

q is zero or an integer from 1 to 4; and s is an integer from 1 to 8.

3. A compound of the claim 2 of the formula $$R_{21}-\overset{O}{\underset{OR_3}{\overset{\|}{P}}}-\overset{R_1}{\underset{}{N}}-\overset{R_2}{\underset{}{CH}}-\overset{O}{\overset{\|}{C}}-N\begin{pmatrix}(CH_2)_t\\Y\overset{}{\diagup\!\!\!\diagdown}Y\\H_2C\quad CH_2\\|\quad\quad|\\ \quad\quad C-COOR_6;\\ \quad\quad|\,\,(L)\\ \quad\quad H\end{pmatrix}$$

wherein:

Y is oxygen or sulfur;

t is two or three; and $R_6$ is hydrogen, $$-\underset{CH_3}{\overset{}{\underset{|}{CH}}}-O-\overset{O}{\overset{\|}{C}}-CH_3, \quad -CH_2-O-\overset{O}{\overset{\|}{C}}-C(CH_3)_3,$$

$$-\underset{CH(CH_3)_2}{\overset{}{\underset{|}{CH}}}-O-\overset{O}{\overset{\|}{C}}-C_2H_5, \quad -\underset{CH_3}{\overset{}{\underset{|}{CH}}}-O-\overset{O}{\overset{\|}{C}}-C_2H_5,$$

$$-\underset{\text{(cyclohexyl)}}{\overset{}{\underset{|}{CH}}}-O-\overset{O}{\overset{\|}{C}}-C_2H_5,$$

or an alkali metal salt.

4. A compound of claim 3 wherein $R_1$ is hydrogen or methyl;

$R_2$ is hydrogen, methyl, or —$(CH_2)_4$—$NH_2$; and $R_3$ is hydrogen, ethyl, $$-\underset{CH_3}{\overset{}{\underset{|}{CH}}}-O-\overset{O}{\overset{\|}{C}}-CH_3, \quad -CH_2-O-\overset{O}{\overset{\|}{C}}-C(CH_3)_3,$$

$$-\underset{CH(CH_3)_2}{\overset{}{\underset{|}{CH}}}-O-\overset{O}{\overset{\|}{C}}-C_2H_5, \quad -\underset{CH_3}{\overset{}{\underset{|}{CH}}}-O-\overset{O}{\overset{\|}{C}}-C_2H_5,$$

$$-\underset{\text{(cyclohexyl)}}{\overset{}{\underset{|}{CH}}}-O-\overset{O}{\overset{\|}{C}}-C_2H_5,$$

or an alkali metal salt.

5. A compound of claim 4 wherein $R_{21}$ is alkyl of 1 to 10 carbons.

6. A compound of claim 4 wherein $R_{21}$ is $$-(CH_2)_q-\!\!\!\bigcirc\!\!\!-R_{13}.$$

q is zero or an integer from 1 to 4, and $R_{13}$ is hydrogen, methyl, methoxy, methylthio, chloro, bromo, fluoro, or hydroxy.

7. A compound of claim 6 wherein X is $$\begin{array}{c}\lceil\quad\quad\rceil\\ S\quad\diagup\!\!\!\diagdown\quad S\\ H_2C\quad\quad CH_2\\ |\quad\quad\quad|\\ -N\quad\quad\quad C-COOR_6.\\ \quad\quad\quad|\,\,(L)\\ \quad\quad\quad H\end{array}$$

8. The compound of claim 7 wherein $R_{21}$ is $$-(CH_2)_4-\!\!\!\bigcirc\!\!\!;$$

$R_1$ is hydrogen;

$R_2$ is methyl;

$R_3$ and $R_6$ are the same and both are hydrogen or an alkali metal salt.

9. A compound of claim 4 wherein $R_{21}$ is —$(CH_2)_s$—$NH_2$ and s is an integer from 1 to 8.

10. A composition useful for treating hypertension in a mammalian specie comprising a pharmaceutically acceptable carrier and an effective amount of a hypotensive agent or pharmaceutically acceptable salt thereof of the formula $$R_{21}-\overset{O}{\underset{OR_3}{\overset{\|}{P}}}-\overset{R_1}{\underset{}{N}}-\overset{R_2}{\underset{}{CH}}-\overset{O}{\overset{\|}{C}}-N\begin{pmatrix}R_{16}\quad\quad R_{16}\\|\quad\quad\quad|\\Y\overset{}{\diagup\!\!\!\diagdown}Y\\H_2C\quad CH_2\\|\quad\quad|\\ \quad\quad C-COOR_6\\ \quad\quad|\,\,(L)\\ \quad\quad H\end{pmatrix}$$

wherein $R_1$, $R_2$, $R_3$, $R_6$, $R_{21}$, Y, and $R_{16}$ are as defined in claim 1.

11. The composition of claim 10 also including a diuretic.

12. The method of alleviating hypertension in a mammalian specie which comprises administering an effective amount of the composition of claim 10.

* * * * *

UNITED STATES PATENT AND TRADEMARK OFFICE
CERTIFICATE OF CORRECTION

PATENT NO. : 4,432,971
DATED : February 21, 1984
INVENTOR(S) : Donald S. Karanewsky et al.

It is certified that error appears in the above-identified patent and that said Letters Patent are hereby corrected as shown below:

Column 3, line 10, third formula should read

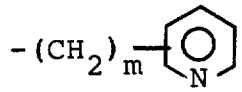

Column 6, line 2, delete "lowr" and insert -- lower --.
Column 6, line 9, third formula should read -CH=CH-;
Column 15, at top of the column, second formula should read

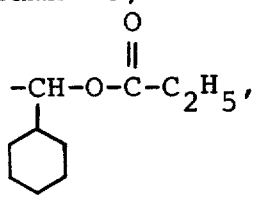

Column 16, at top of the column, second formula should read

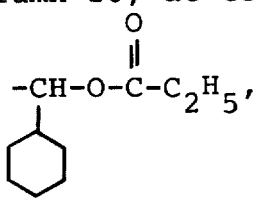

Column 19, line 24, delete "persits" and insert -- persists --.

UNITED STATES PATENT AND TRADEMARK OFFICE
CERTIFICATE OF CORRECTION

PATENT NO. : 4,432,971

DATED : February 21, 1984

INVENTOR(S) : Donald S. Karanewsky et al.

It is certified that error appears in the above-identified patent and that said Letters Patent are hereby corrected as shown below:

Column 35, line 29, delete "(5.3)" and insert -- (5/3) --.
Column 39, line 38, delete "timethylsilylbromide" and insert
-- trimethylsilylbromide --.
Column 41, line 34, delete "Dimethylthoxy)" and insert
-- Dimethylethoxy) --.
Col. 61, Example 56, under X, the top portion of the formula should be

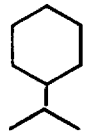

Column 62, Example 58, the formula under $R_{21}$ should read

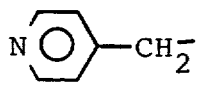

Column 80, Example 98, the formula under $R_{21}$ should be

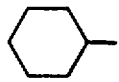

UNITED STATES PATENT AND TRADEMARK OFFICE
CERTIFICATE OF CORRECTION

PATENT NO.  : 4,432,971
DATED       : February 21, 1984
INVENTOR(S) : Donald S. Karanewsky et al.

It is certified that error appears in the above-identified patent and that said Letters Patent are hereby corrected as shown below:

Column 89, line 2, delete "Similrly" and insert -- Similarly --.
Column 99, line 64, the formula after or should read

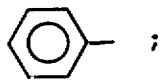

Column 100, line 4, the formula should read

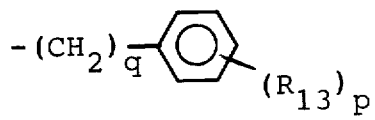

Column 100, line 14, the second formula should read

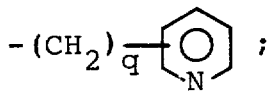

Signed and Sealed this

Nineteenth Day of November 1985

[SEAL]

Attest:

DONALD J. QUIGG

Attesting Officer

Commissioner of Patents and Trademarks